US011320429B1

(12) United States Patent
Strongin et al.

(10) Patent No.: US 11,320,429 B1
(45) Date of Patent: May 3, 2022

(54) DIAGNOSTIC DEVICES WITH FLUID RESERVOIRS AND ASSOCIATED METHODS AND KITS

(71) Applicant: Global Diagnostic Systems, Benefit LLC, Potomac, MD (US)

(72) Inventors: Wendy Strongin, Potomac, MD (US); Elliott Millenson, Potomac, MD (US); Carolyn S. Millenson, Potomac, MD (US); Weiwei Wu, Shanghai (CN); Yingmin Fu, Shanghai (CN); Shengcheng Fu, Shanghai (CN); Kuang-hsu Cheng, Shanghai (CN); William David Postle, Queens Park (AU); David Andrew Jones, Beecroft (AU); Giovanni Ciampa, Ryde (AU); Siao Hau Teh, Telopea (AU)

(73) Assignee: Global Diagnostic Systems, Benefit LLC, Potomac, MD (US)

( * ) Notice: Subject to any disclaimer, the term of this patent is extended or adjusted under 35 U.S.C. 154(b) by 0 days.

(21) Appl. No.: 17/204,756

(22) Filed: Mar. 17, 2021

(30) Foreign Application Priority Data

Mar. 5, 2021 (CN) .......................... 202110249671.1

(51) Int. Cl.
*G01N 33/543* (2006.01)
*G01N 33/569* (2006.01)

(52) U.S. Cl.
CPC . *G01N 33/54386* (2013.01); *G01N 33/56983* (2013.01); *G01N 2333/165* (2013.01)

(58) Field of Classification Search
CPC ....... G01N 33/54386; G01N 33/56983; G01N 2333/165
See application file for complete search history.

(56) References Cited

U.S. PATENT DOCUMENTS

| 5,091,153 | A | * | 2/1992 | Bachand | ............. | G01N 33/523 422/411 |
| 5,173,433 | A | * | 12/1992 | Bachand | ............. | G01N 33/523 422/411 |
| 7,114,403 | B2 | | 10/2006 | Wu et al. | | |
| 9,791,437 | B2 | | 10/2017 | Egan et al. | | |
| 10,317,404 | B2 | | 6/2019 | Campbell et al. | | |
| 2002/0004019 | A1 | * | 1/2002 | Bachand | ............... | B01L 3/5029 422/411 |
| 2002/0085958 | A1 | | 7/2002 | Nemcek et al. | | |
| 2004/0184954 | A1 | * | 9/2004 | Guo | ..................... | B01L 3/5023 422/400 |
| 2005/0106753 | A1 | | 5/2005 | Wu et al. | | |
| 2008/0199851 | A1 | * | 8/2008 | Egan | ..................... | B01L 3/5029 435/5 |
| 2010/0022916 | A1 | | 1/2010 | Esfandiari | | |
| 2010/0261157 | A1 | | 10/2010 | Brock | | |
| 2017/0227536 | A1 | * | 8/2017 | Matsuura | ............. | G01N 1/4055 |
| 2018/0339292 | A1 | | 11/2018 | Katz et al. | | |
| 2019/0086380 | A1 | * | 3/2019 | Harding | ............. | G01N 21/8483 |
| 2019/0142642 | A1 | * | 5/2019 | Burnet | .............. | A61F 13/00051 600/362 |
| 2020/0278368 | A1 | * | 9/2020 | Hopper | .................... | C12N 1/06 |
| 2020/0383664 | A1 | * | 12/2020 | Loudermilk | .......... | B01L 3/5029 |

FOREIGN PATENT DOCUMENTS

DE   202020102077 U1   6/2020
EP       1847321 A1   10/2007

OTHER PUBLICATIONS

Becton, Dickinson and Company, "BD Veritor System for Rapid Detection of SARS-CoV-2" test package insert, Aug. 2020, 17 pgs.
Access Bio Inc., "Rapid Diagnostic Test for the Detection of SARS-CoV-2 Antigen", Sep. 23, 2020, 20pgs.
Abbott Diagnostics Scarborough, Inc., "BinaxNOWTM COVID-19 Ag Card Home Test", (https://www.fda.gov/media/144574/download). Dec. 2020, 17pgs.
International Search Authority, International Search Report and Written Opinion for Application No. PCT/US2021/022819, dated Nov. 5, 2021, 14 pages.

* cited by examiner

*Primary Examiner* — Ann Montgomery
(74) *Attorney, Agent, or Firm* — Perkins Coie LLP

(57) ABSTRACT

Devices and associated methods for analyzing patient samples are disclosed herein. In some embodiments, a device includes a housing base configured to retain a test strip, and a housing cover configured to couple to the housing base to at least partially enclose the test strip. The housing cover can include a fluid reservoir configured to hold a solution for hydrating a sample swab. The housing can further include an aperture configured to permit transfer of a sample from the sample swab onto the test strip.

27 Claims, 23 Drawing Sheets

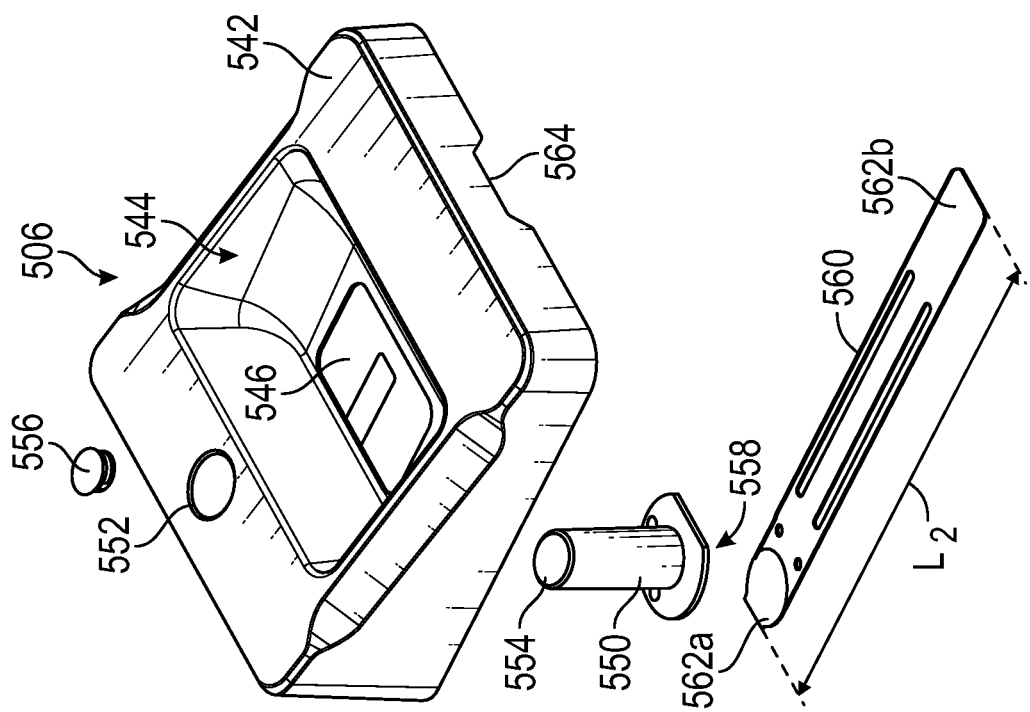
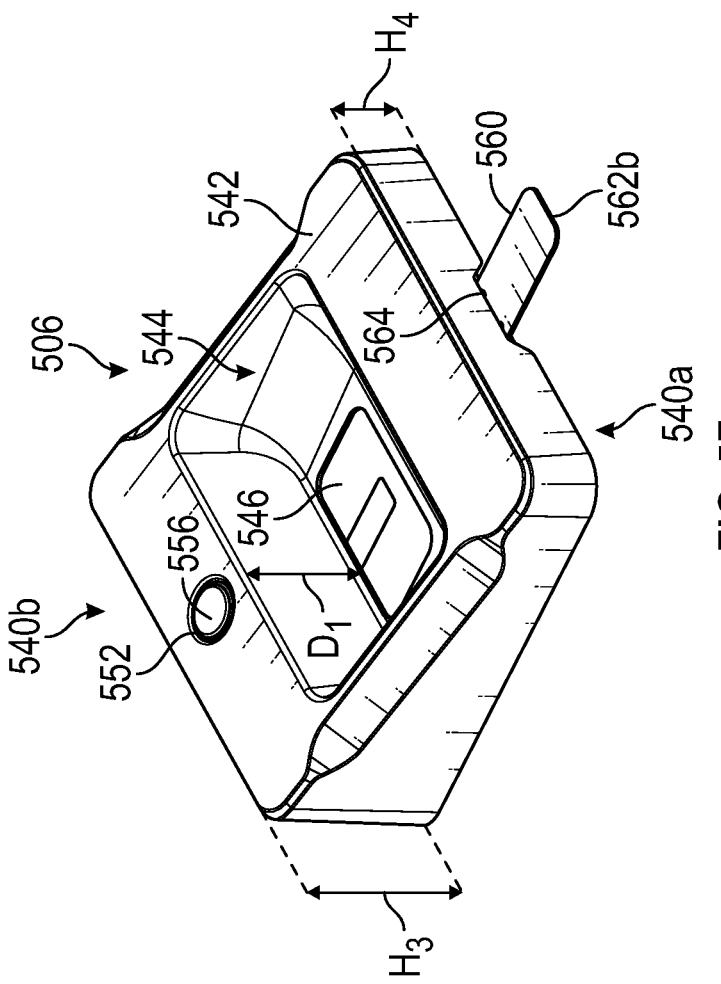
FIG. 5F
FIG. 5G

DIAGNOSTIC DEVICES WITH FLUID RESERVOIRS AND ASSOCIATED METHODS AND KITS

CROSS-REFERENCE TO RELATED APPLICATIONS

The present application claims priority to Chinese Patent Application No. 202110249671.1, filed Mar. 5, 2021, which is incorporated by reference herein in its entirety.

TECHNICAL FIELD

The present technology generally relates to medical devices and, in particular, to diagnostic devices and associated methods and kits for analyzing patient samples.

BACKGROUND

The worldwide pandemic caused by the spread of COVID-19 has killed over 1,400,000 persons worldwide as of November 2020. It has also impaired the quality of life of many others and had significant social and economic impacts across the world. Diagnostic testing for infection is central to detecting the virus in persons presenting with and without COVID-19 symptoms and those who have been in contact with persons exposed to COVID-19 to contain the spread of the virus. Diagnostic testing will continue to be important as it is expected the virus will continue to circulate for at least the next several years even with the availability of vaccines.

Current diagnostic testing requires individuals to go to testing sites and provide a sample, which is usually a specimen from the nasopharynx or oropharynx. For example, the reverse transcriptase polymerase chain reaction (RT-PCR) test is the predominant test used to detect COVID-19 with a high degree of accuracy. Other tests include rapid antigen tests, which are most accurate during the period when the viral load is highest and therefore most infectious. Both tests are inconvenient and expose both the person being tested and the person taking the nasal swab sample to possible infection. Therefore, there is a strong need for a low-cost, easy to use, accurate test that can be performed by the person being tested in private and that provides the results quickly.

BRIEF DESCRIPTION OF THE DRAWINGS

FIG. 5F is a perspective view of a housing cover of the device of FIG. 5A.

FIG. 5G is an exploded view of the housing cover of FIG. 5F.

FIGS. 5J-5O illustrate a process for operating the device of FIG. 5A, in accordance with embodiments of the present technology.

DETAILED DESCRIPTION

Figure 1A:
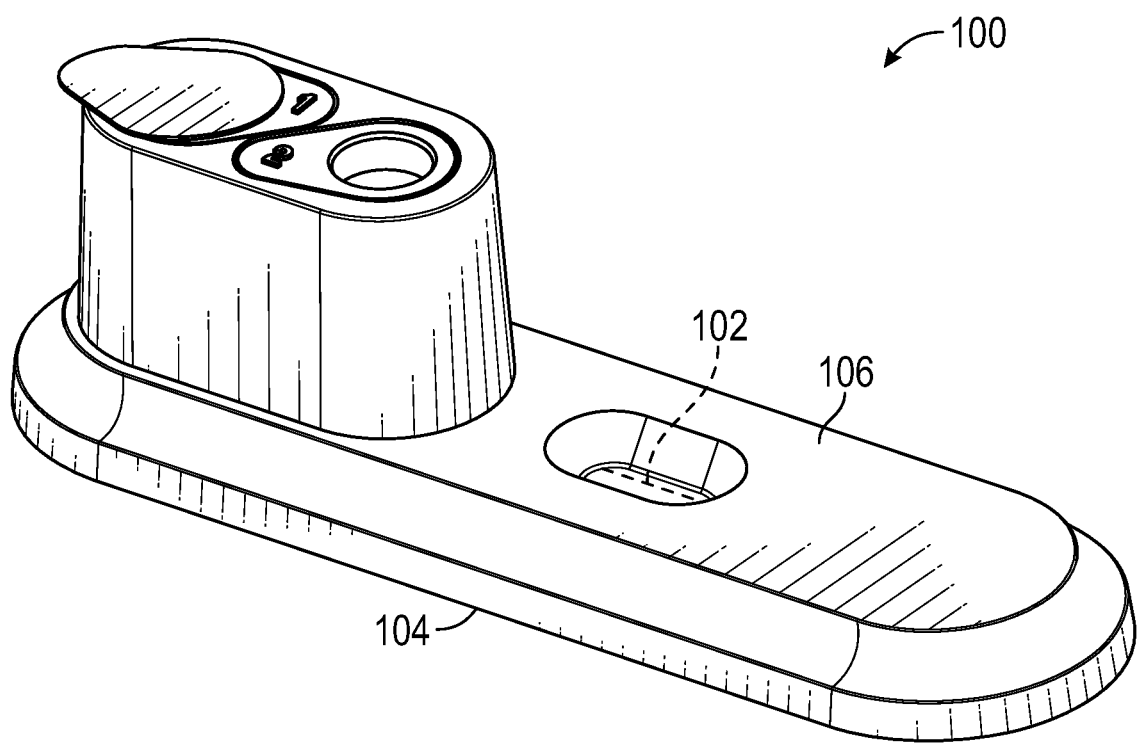
FIG. 1A is a perspective view of a diagnostic device for analyzing a patient sample configured in accordance with embodiments of the present technology.

The present technology is directed to devices and associated methods and kits for analyzing a patient sample to diagnose the patient with a disease or condition, such as COVID-19. In some embodiments, for example, a device for analyzing a sample includes a housing base configured to retain a test strip (e.g., a lateral flow immunoassay (LFA) test strip), and a housing cover configured to couple to the housing base to enclose the test strip. The housing cover can include a fluid reservoir configured to hold a solution for hydrating the sample swab, eluting a sample from the sample swab, and/or otherwise interacting with the sample (e.g., a buffer solution, lysing solution, reagent solution, etc.). In contrast to conventional diagnostic kits that provide assay solutions in separate vials or bottles, the devices with integrated fluid reservoirs disclosed herein are expected to be more convenient and easier for laypersons to use.

In some embodiments, the devices disclosed herein are designed to receive a sample directly from the sample swab, rather than from a pipette, dropper bottle, etc. For example, the housing cover of the device can include an aperture configured to expose a portion of the test strip so the sample can be transferred from the sample swab onto the test strip. In some embodiments, the aperture is spaced apart from the fluid reservoir and configured to receive the sample swab. The aperture can direct the sample swab into direct contact with the test strip to transfer the sample onto the test strip. Optionally, the housing can include a guide structure at or near the aperture to facilitate proper contact between the sample swab and the test strip. In some embodiments, the guide structure is or includes a stop surface that engages a portion of the sample swab (e.g., the handle) to control the insertion depth and/or angle of the sample swab.

In some embodiments, the aperture can be at a bottom portion of the fluid reservoir and above a portion of the test strip. In such embodiments, the device can further include a removable sealing element covering the aperture and separating the fluid reservoir from the test strip. To use the device, a user can insert the sample swab into the fluid reservoir to elute the sample from the sample swab. The user can then remove the sealing element from the device to uncover the aperture in the bottom portion of the fluid reservoir and allow the eluted sample to flow onto the test strip.

The present technology provides low-cost, reliable diagnostic devices suitable for use in a private setting (e.g., in the patient's home) as well as in laboratories, doctor's offices, clinics, schools, airports, restaurants, and/or other point of care and/or high traffic public settings. The devices can be sufficiently simple and easy to use such that laypersons (e.g., the patient undergoing testing) can perform diagnostic testing without assistance from a healthcare professional. Additionally, the devices described herein are expected to be low-cost and suitable for mass distribution to large numbers of consumers, thus allowing for large-scale, rapid testing for infectious diseases (e.g., COVID-19) and/or other conditions. In some embodiments, the devices and methods described herein use antigen-based tests, which can provide faster results compared to other types of tests (e.g., PCR tests). Accordingly, the patient can quickly determine whether they are positive and can take immediate action to limit the spread of infection (e.g., quarantine) and/or seek treatment.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-6.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Figure 1B:
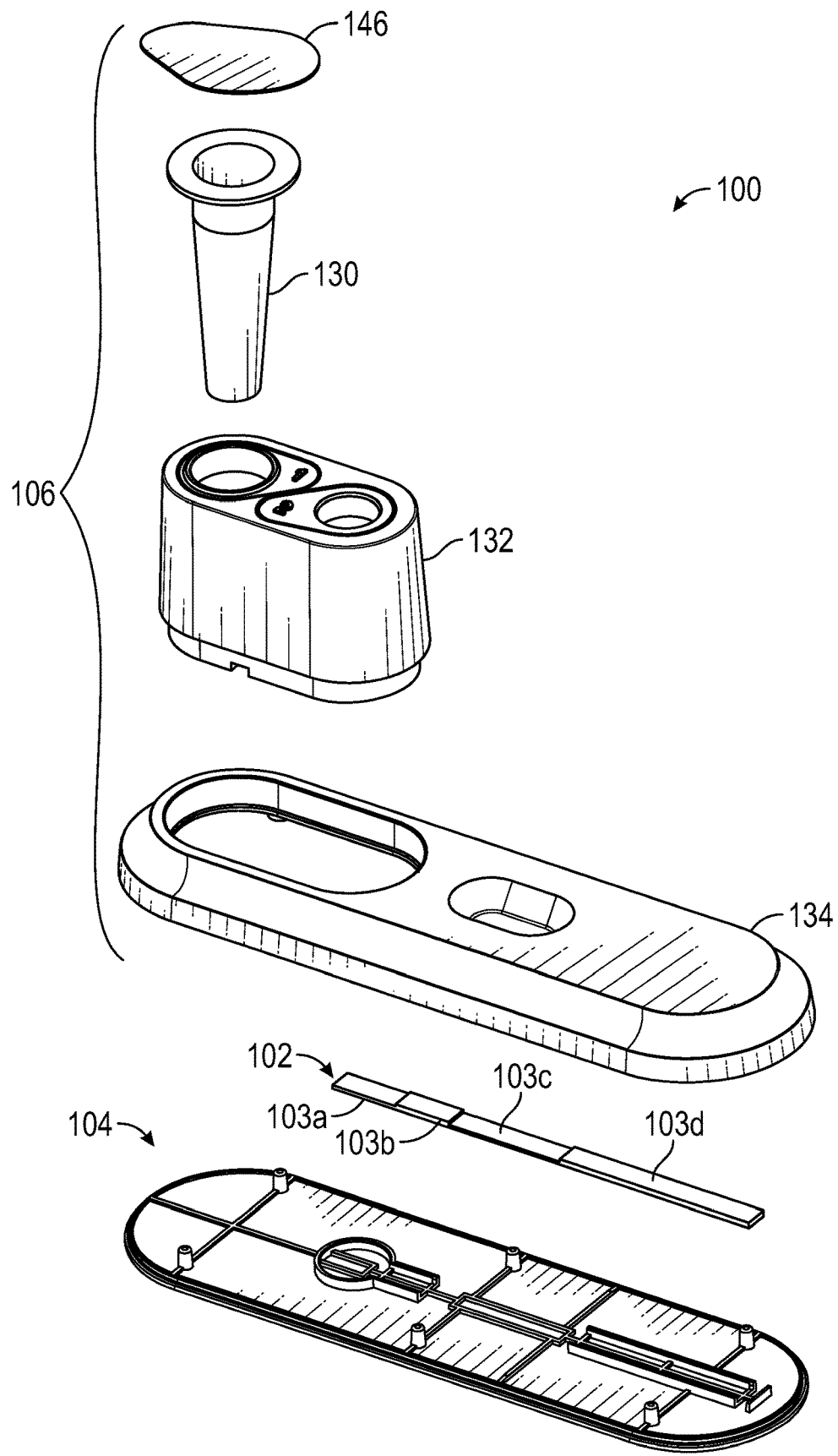
FIG. 1B is an exploded view of the device of FIG. 1A.
Figure 1C:
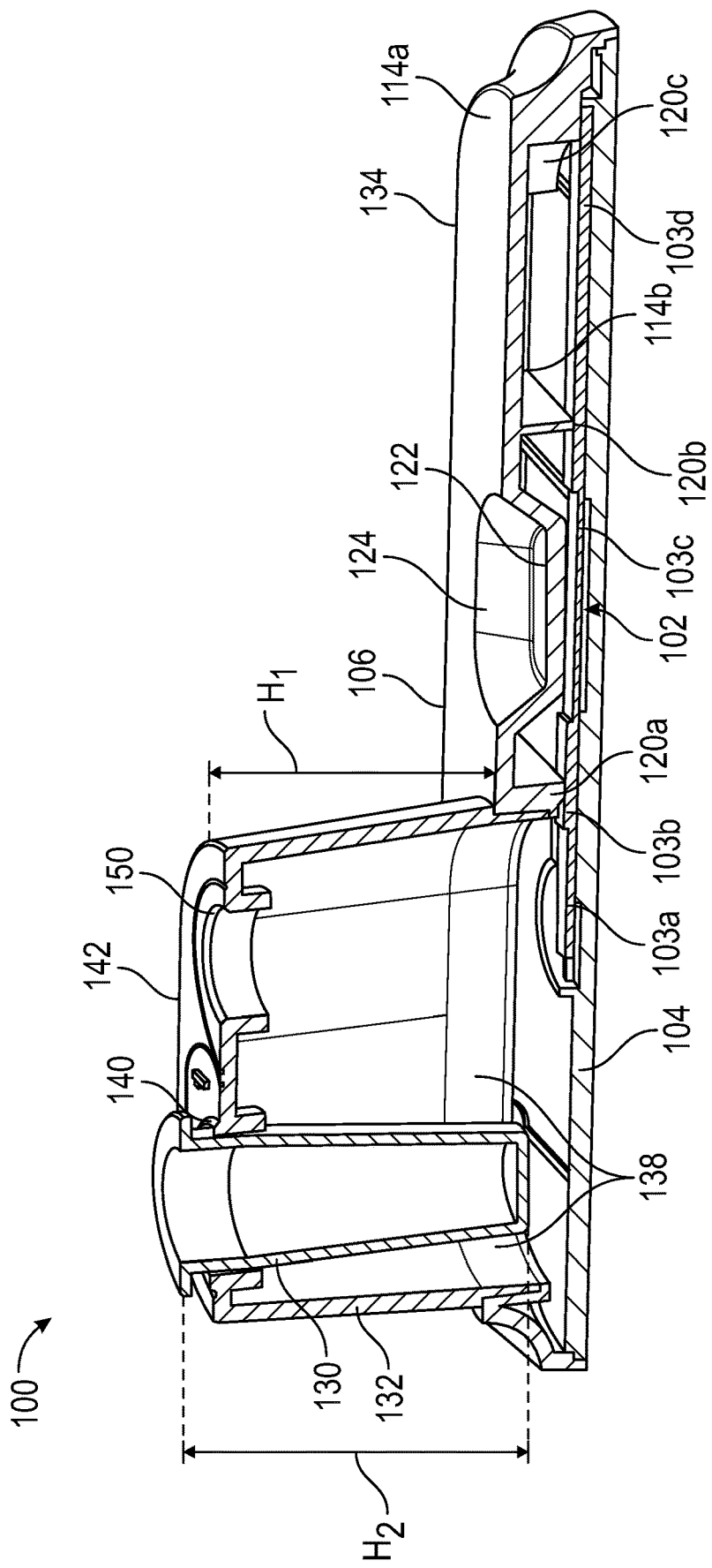
FIG. 1C is a cross-sectional view of the device of FIG. 1A.

FIGS. 1A-1G illustrate a diagnostic device 100 ("device 100") for analyzing a patient sample configured in accordance with embodiments of the present technology. Specifically, FIG. 1A is a perspective view of the device 100, FIG. 1B is an exploded view of the device 100, FIG. 1C is a cross-sectional view of the device 100, and FIGS. 1D-1G are various views of individual components of the device 100.

Referring first to FIGS. 1A-1C together, the device 100 can be a test cassette, cartridge, or similar structure for housing a test strip 102 (best seen in FIGS. 1B and 1C). In some embodiments, the device 100 is configured to receive a patient sample from a sample swab and detect at least one analyte (e.g., SARS-CoV-2 virus or a component thereof) in the sample via the test strip 102. As described in detail below, the device 100 can be simpler to operate and can require fewer components than devices that receive sample droplets from a dropper bottle, pipette, etc.

As best seen in FIG. 1B, the test strip 102 can be a nitrocellulose test strip or similar test strip suitable for use in an LFA procedure. The test strip 102 can be configured in accordance with techniques known to those of skill in the art. For example, in the illustrated embodiment, the test strip 102 includes a sample pad portion 103a, a conjugate pad portion 103b, a detection or readout portion 103c, and/or a wicking pad portion 103d. The sample pad portion 103a can include an absorbent material configured to receive a fluid sample. The conjugate pad portion 103b can include a detectable reagent (e.g., a detection antibody) configured to bind to an analyte in the sample. The readout portion 103c can include a test line with a first reagent (e.g., a capture antibody) that binds to the analyte, and a control line with a second reagent (e.g., a secondary antibody) that binds to the detectable reagent. The wicking pad portion 103d can include an absorbent material for absorbing fluid.

The device 100 includes a housing configured to partially or fully enclose the test strip 102. The housing can include a housing base 104 configured to receive the test strip 102, and a housing cover 106 configured to couple to the housing base 104. When assembled, the housing base 104 forms the lower portion of the device 100 and the housing cover 106 forms the upper portion of the device 100. The housing base 104 and housing cover 106 can be made of any suitable material (e.g., plastic), and can be transparent, translucent, or opaque, as desired. The features of the housing base 104 and housing cover 106 are described in detail below with reference to FIGS. 1D-1G.

Figure 1D:
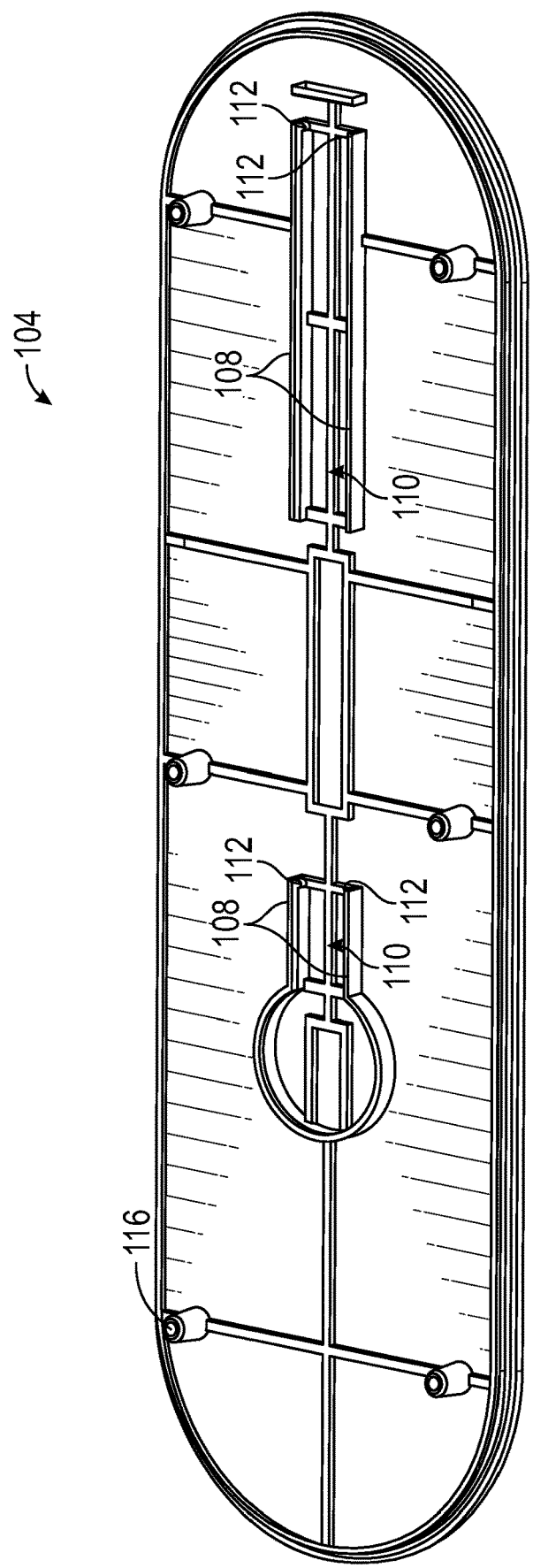
FIG. 1D is a top perspective view of a housing base of the device of FIG. 1A.

FIG. 1D is a top perspective view of the housing base 104. The housing base 104 can have an elongate, generally flattened shape. Although FIG. 1D depicts the housing base 104 as having an oval shape with flattened sides, in other embodiments the housing base 104 can have a different shape (e.g., oval, rectangular, etc.). The housing base 104 can include various structures for supporting and/or securing the test strip 102 (the test strip 102 is omitted from FIG. 1D for clarity). In the illustrated embodiment, for example, the housing base 104 includes a set of walls 108 (e.g., continuous or discontinuous walls) defining an elongate channel 110 for receiving the test strip 102. The geometry of the elongate channel 110 can be substantially similar to the geometry of the test strip (e.g., with respect to length and/or width). Optionally, the walls 108 can include one or more protrusions 112 that engage (e.g., compress) the test strip 102 to constrain it to a fixed position within the elongate channel 110. The protrusions 112 can be at any suitable location along the elongate channel 110, such as at or near the ends of the elongate channel 110, at or near the central section of the elongate channel 110, and/or combinations thereof.

Figure 1E:
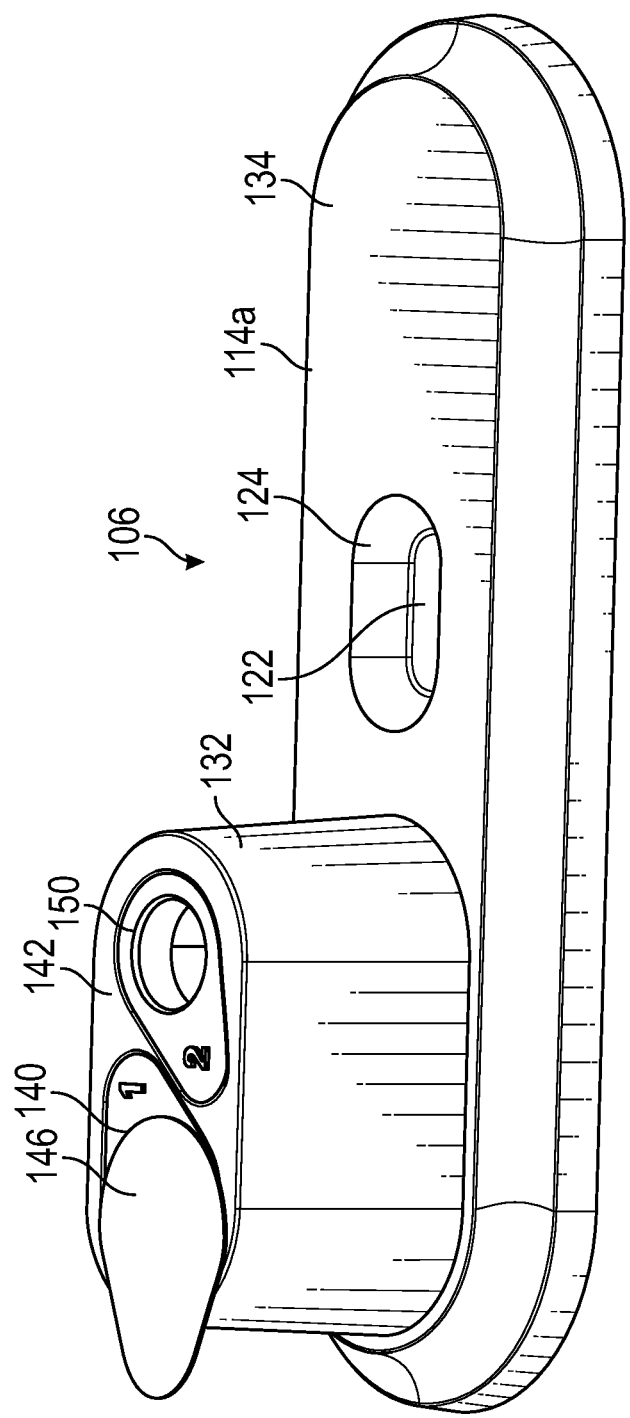
FIG. 1E is a top perspective view of a housing cover of the device of FIG. 1A.
Figure 1F:
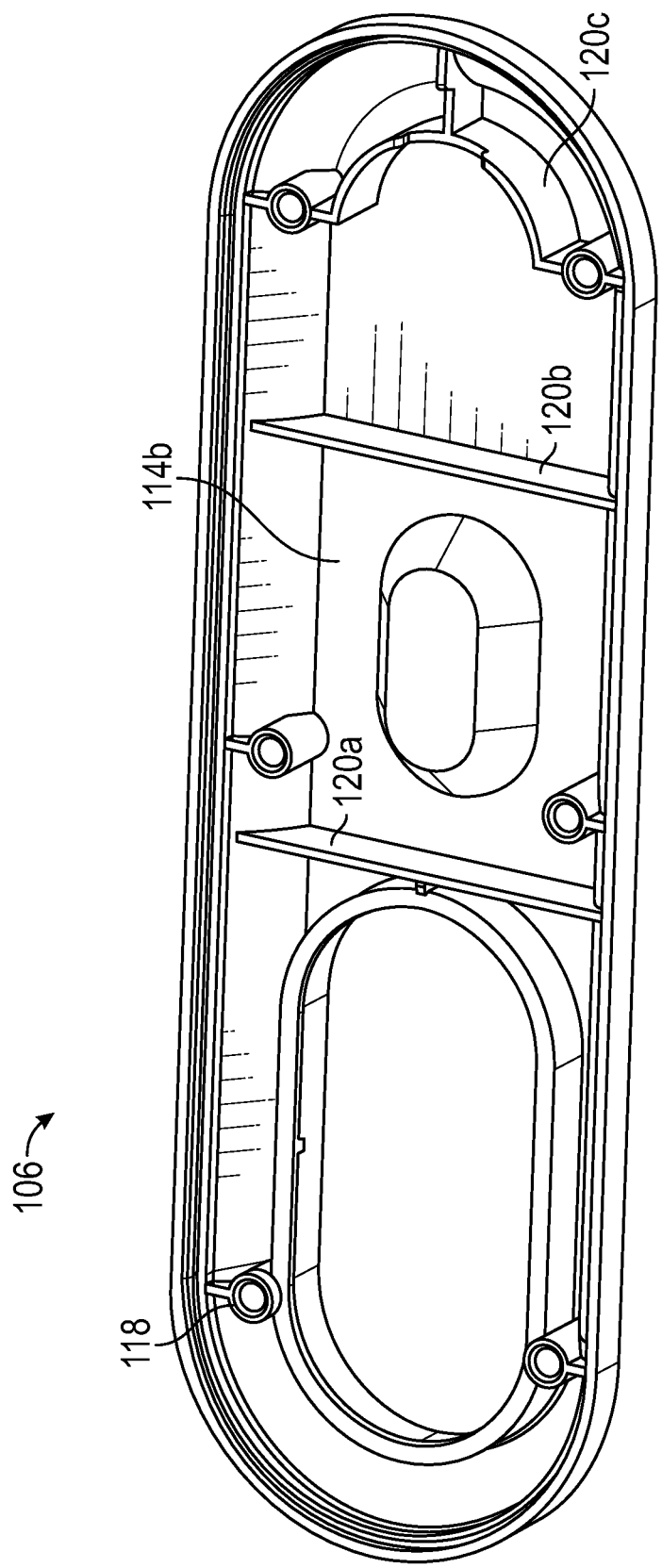
FIG. 1F is a bottom perspective view of the housing cover of FIG. 1E.
Figure 1G:
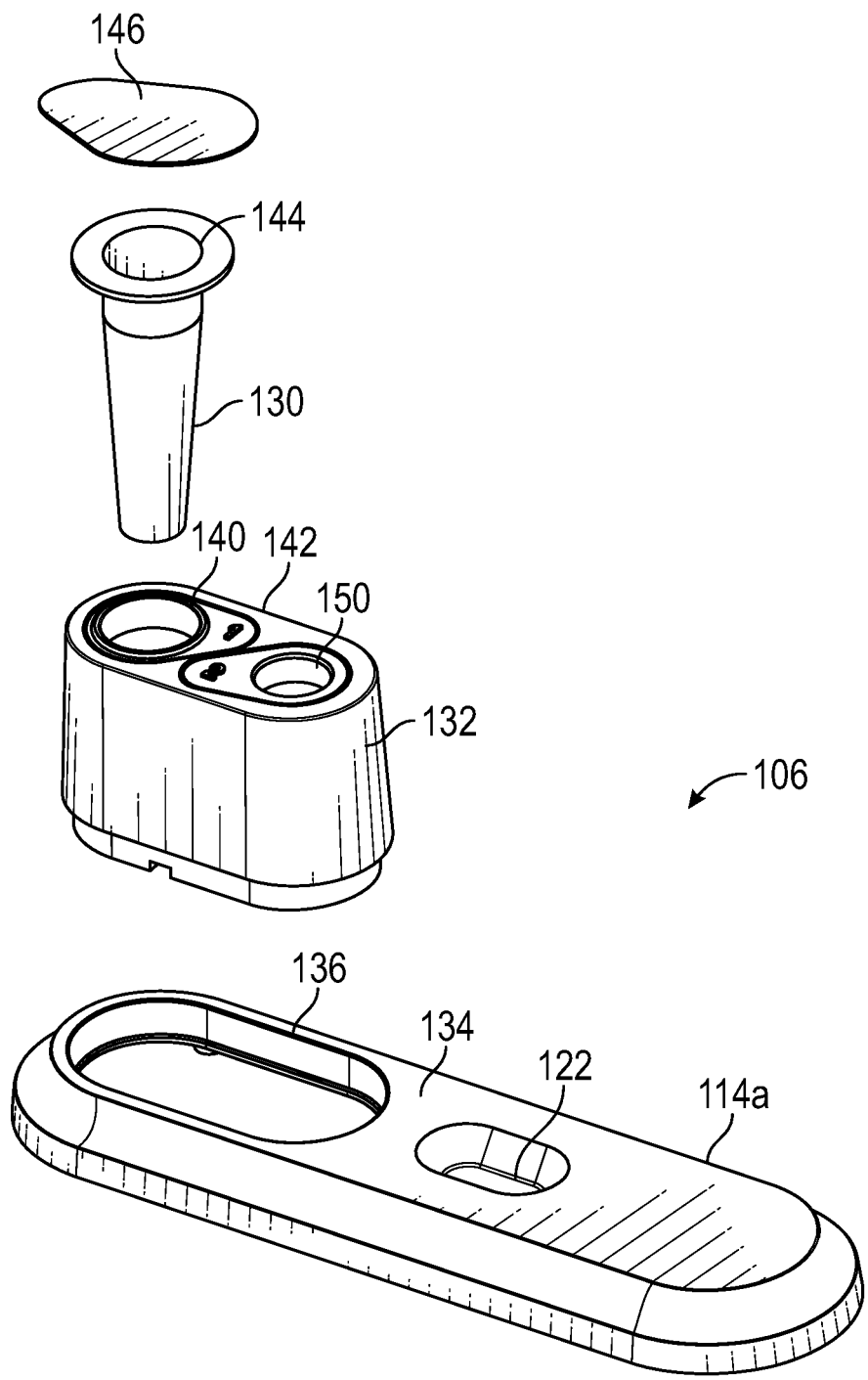
FIG. 1G is an exploded view of the housing cover of FIG. 1E.

FIGS. 1E-1G are top perspective (FIG. 1E), bottom perspective (FIG. 1F), and exploded (FIG. 1G) views of the housing cover 106. The housing cover 106 can have an elongate shape, e.g., similar to the shape of the housing base 104. The housing cover 106 includes an outer surface 114a facing away from the test strip 102 (FIGS. 1E and 1G) and an inner surface 114b facing toward the test strip 102 (FIG. 1F).

Referring to FIGS. 1D and 1F together, the housing cover 106 is configured to couple to the housing base 104 to enclose and protect the test strip 102. The housing cover 106 and housing base 104 can be coupled using any suitable technique, such as interference fit, snap fit, adhesives, bonding, fasteners, and the like. In the illustrated embodiment, for example, the housing base 104 includes a set of posts 116 (FIG. 1D), and the housing cover 106 includes a corresponding set of receptacles 118 on its inner surface 114b (FIG. 1F).

Each post 116 fits into a corresponding receptacle 118 to connect the housing base 104 to the housing cover 106. In other embodiments, this arrangement can be reversed, such that the posts 116 are located on the housing cover 106 and the receptacles 118 are located on the housing base 104. Additionally, although FIGS. 1D and 1F illustrate six posts 116 and receptacles 118, in other embodiments, the housing base 104 and housing cover 106 can include fewer or more posts 116 and receptacles 118, respectively.

As shown in FIG. 1F, the inner surface 114b of the housing cover 106 can also include one or more structures configured to contact the test strip 102, e.g., to secure the test strip 102 and/or enhance fluid flow through the test strip 102. In the illustrated embodiment, for example, the inner surface 114b includes a plurality of struts or walls, such as a first strut 120a, a second strut 120b, and a third strut 120c. The first and second struts 120a-b can be linear, while the third strut 120c can be curved. In other embodiments, however, the number, arrangement, and/or geometries of the struts 120a-c can be varied as desired.

Referring again to FIG. 1C, when the housing cover 106 is connected to the housing base 104, the struts 120a-c can be adjacent or near different portions of the test strip 102, e.g., the first and third struts 120a, 120c are near the ends of the test strip 102, while the second strut 120b is near the middle of the test strip 102. In some embodiments, the first strut 120a contacts the conjugate pad portion 103b of the test strip 102, and the second and third struts 120b-c contact the wicking pad portion 103d of the test strip 102. In other embodiments, however, the struts 120a-c can contact different portions of the test strip 102, and/or one or more of the struts 120a-c can be omitted.

Referring next to FIGS. 1C and 1E together, the housing cover 106 can include a window 122 for viewing the readout portion 103c of the test strip 102. The window 122 can be made of a transparent or translucent material to expose the test strip 102 so the user can view the assay results. In the illustrated embodiment, the window 122 is within a recess 124 in the upper surface 114a of the housing cover 106. The window 122 can be a generally flat structure that contacts the test strip 102 (best seen in FIG. 1C), which can further enhance fluid flow through the test strip 102. The window 122 can optionally be or include a lens having a magnification to enhance readability of the results. Although the window 122 is depicted as having an oval shape, in other embodiments, the window 122 can have a different shape (e.g., circular, rectangular, etc.).

Referring next to FIG. 1G, the housing cover 106 can include a fluid reservoir 130 (e.g., a tube, vial, chamber, etc.) configured to hold a solution. The solution within the fluid reservoir 130 can be any fluid used in an LFA procedure, such as a buffer solution, reagent solution, lysing solution, wash solution, etc. For example, the solution can be used to hydrate a sample swab to facilitate sample transfer onto the test strip 102, as described further below. Alternatively or in combination, the solution can include one or more reagents configured to react with an analyte in the sample, e.g., for purposes of analyte detection. In some embodiments, for example, the solution includes a lysing agent configured to lyse viruses, bacteria, cells, etc., to release the analyte of interest. The fluid reservoir 130 can be configured to hold any suitable volume of solution, such as at least 50 μL, 75 μL, 100 μL, 200 μL, 300 μL, 400 μL, 500 μL, 600 μL, 700 μL, 800 μL, 900 μL, or 1 mL.

The fluid reservoir 130 can be integrated with or otherwise connected to the housing cover 106 such that the fluid reservoir 130 cannot be separated from the housing cover 106 without destroying the device 100. In the illustrated embodiment, for example, the fluid reservoir 130 is a separate component (e.g., a tube or vial) that is permanently affixed to the housing cover 106 during the manufacturing process (e.g., by bonding, adhesives, interference fit, snap fit, etc.). In other embodiments, however, the fluid reservoir 130 can be integrally formed with the housing cover 106 as a single unitary component.

The fluid reservoir 130 can be at any suitable location in the housing cover 106. In the illustrated embodiment, for example, the housing cover 106 includes a raised portion 132 and flattened portion 134, and the fluid reservoir 130 is in the raised portion 132. The raised portion 132 can be at or near an end of the housing cover 106, and the flattened portion 134 can form the remaining part of the housing cover 106. As shown in FIG. 1G, the raised portion 132 can be a separate piece that fits into a corresponding opening 136 in the flattened portion 134 to assemble the housing cover 106. In such embodiments, the raised portion 132 can be permanently affixed to the flattened portion 134 via bonding, adhesives, interference fit, snap fit, and the like. In other embodiments, however, the raised portion 132 and the flattened portion 134 can be integrally formed as a single unitary component.

Referring again to FIG. 1C, the raised portion 132 can be a hollow structure defining an interior cavity or space 138. The fluid reservoir 130 can be a tube, vial, chamber, etc., that fits within the interior cavity 138, e.g., via an opening 140 in an upper surface 142 of the raised portion 132. The fluid reservoir 130 can be a separate component that is fixedly attached to the raised portion 132, or the fluid reservoir 130 can be integrally formed with the raised portion 132. The geometry of the raised portion 132 (e.g., shape, height, volume, etc.) can be configured to accommodate the fluid reservoir 130. In some embodiments, for example, the height $H_1$ of the raised portion 132 above the flattened portion 134 is at least 0.25 cm, 0.5 cm, 1 cm, 1.5 cm, 1.75 cm, 2 cm, 2.25 cm, or 2.5 cm; and/or is within a range from 1.5 cm to 2.5 cm. The height $H_2$ of the fluid reservoir 130 can be at least 0.5 cm, 1 cm, 1.5 cm, 1.75 cm, 2 cm, 2.25 cm, 2.5 cm., 2.75 cm, 3 cm, 3.25 cm, or 3.5 cm; and/or can be within a range from 2.5 cm to 3.5 cm. The raised portion 132 can have a length of at least 1 cm, 2 cm, 3 cm, 4 cm, or 5 cm; and/or can have a width of at least 0.5 cm, 1 cm, 1.5 cm, 2 cm, or 2.5 cm. In the illustrated embodiment, the horizontal cross-sectional shape of the raised portion 132 is an oval with flattened sides. In other embodiments, the horizontal cross-sectional shape can be circular, oval, square, rectangular, or any other suitable shape.

As best seen in FIG. 1G, the fluid reservoir 130 can include an opening or aperture 144 so that the sample swab can access the fluid reservoir 130. The opening 144 can have any suitable geometry. For example, although FIG. 1G depicts the opening 144 as being circular, in other embodiments, the opening 144 can be oval, square, rectangular, or any other suitable shape. Additionally, the opening 144 can have a diameter or width less than or equal to 0.25 cm, 0.5 cm, 0.75 cm, 1 cm, or 1.5 cm. Optionally, before use, the opening 144 can be covered with a sealing element 146 (e.g., a foil or plastic seal) to contain the solution and/or maintain sterility. The sealing element 146 can include a pull tab or similar feature so the user can manually remove the sealing element 146. In some embodiments, the sealing element 146 also includes labeling, instructions, and/or other markings, e.g., to direct the user to remove the seal and insert the sample swab into the fluid reservoir 130.

Although the illustrated embodiment includes a single fluid reservoir 130, in other embodiments, the device 100 can include multiple fluid reservoirs 130 (e.g., two, three, four, or more fluid reservoirs 130). In such embodiments, each fluid reservoir 130 can hold a different solution, e.g., a first fluid reservoir 130 can hold a buffer solution, a second fluid reservoir 130 can hold a lysing solution, and so on. The geometry of the raised portion 132 can be modified accordingly to accommodate multiple fluid reservoirs 130.

In some embodiments, the housing cover 106 also includes an aperture 150 configured to receive the sample swab and direct the sample swab into direct contact with the test strip 102. When the sample swab directly contacts the test strip 102, the sample on the sample swab can be eluted onto the test strip via capillary action. Sample transfer via direct contact can be advantageous in that it does not require additional transfer devices (e.g., dropper bottles, pipettes) and is easy for a layperson to perform. The efficacy of sample transfer via direct contact can be at least comparable to sample transfer via other techniques. Additionally, the transferred sample can be more concentrated due to the lower fluid volume involved, which can be advantageous for more accurate analyte detection.

The aperture 150 can be at any suitable location in the housing cover 106. For example, the aperture 150 can be aligned with a portion of the test strip 102 (e.g., the sample pad portion 103a of the test strip 102—FIG. 1C) so that the test strip 102 is exposed for access by the sample swab. Optionally, before use, the aperture 150 can be covered by a sealing element (e.g., identical or similar to the sealing element 146), e.g., to maintain sterility of the test strip 102. In the illustrated embodiment, the aperture 150 is in the upper surface 142 of the raised portion 132 of the housing cover, directly above the end of the test strip 102. The aperture 150 can be spaced apart from the fluid reservoir 130, e.g., by at least 0.25 cm, 0.5 cm, 0.75 cm, 1 cm, 1.5 cm, 2 cm, or more. The upper surface 142 of the raised portion 132 can include markings (e.g., "1," "2") directing the user to first insert the sample swab into the fluid reservoir 130 to hydrate the swab, and then insert the sample swab into the aperture 150 to transfer the hydrated sample to the test strip. In other embodiments, however, the aperture 150 can be at a different location, e.g., on the flattened portion 134 of the housing cover 106.

The geometry of the aperture 150 can be configured in many different ways. For example, although the illustrated embodiment depicts the aperture 150 as being circular, in other embodiments, the aperture 150 can be oval, square, rectangular, or any other suitable shape. Additionally, the aperture 150 can have a diameter or width less than or equal to 0.25 cm, 0.5 cm, 0.75 cm, 1 cm, or 1.5 cm. In the embodiment of FIG. 1C, the aperture 150 connects directly to the interior cavity 138 of the raised portion 132. In other embodiments, however, the raised portion 132 can include interior walls defining a discrete channel or lumen for the sample swab to pass through. In such embodiments, the interior walls can optionally include extraction structures (e.g., ribs, protrusions, texturing, etc.) to contact and/or compress the sample swab to enhance sample elution.

In some embodiments, the housing cover 106 includes at least one guide structure configured to direct the sample swab into direct contact with the test strip 102. The guide structure can limit the insertion depth of the sample swab into the aperture 150 to position the sample swab at desired elevation with respect to the test strip 102 (e.g., to limit the amount of contact force between the sample swab and the test strip 102). For example, the guide structure can limit the insertion depth to no more than 0.25 cm, 0.5 cm, 1 cm, 1.5 cm, 1.75 cm, or 2 cm into the device 100. Additionally, the guide structure can assist the user in aligning the sample swab at an appropriate insertion angle to position the sample swab at a desired angular orientation relative to the test strip 102. For example, the guide structure can restrict the sample swab to a vertical or substantially vertical orientation, such that when the sample swab contacts the test strip 102, the angle between the sample swab and the test strip 102 is greater than or equal to 75°, 80°, 85°, or 90°. The guide structure can accordingly position the sample swab at a desired position relative to the test strip 102 to enhance the amount of sample transferred onto the test strip 102 and/or reduce the likelihood of the user inadvertently damaging the sample swab and/or test strip 102.

The guide structure can be configured in many different ways. In the illustrated embodiment, for example, the upper surface 142 of the raised portion 132 surrounding the aperture 150 serves as the guide structure. The upper surface 142 can act as a stop that engages a corresponding portion of the sample swab (e.g., a handle portion—described in greater detail with reference to FIGS. 2 and 3 below) to control the insertion depth and/or insertion angle of the sample swab. Optionally, the portions of the upper surface 142 around the aperture 150 can be shaped to mate with the corresponding portion of the sample swab, e.g., via beveling, grooves, protrusions, etc.

Figure 2:
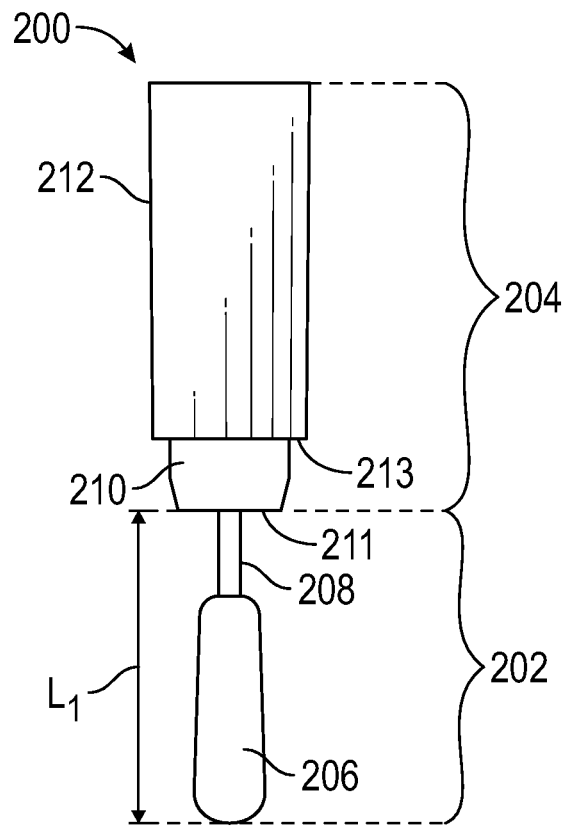
FIG. 2 is a front view of a sample swab configured in accordance with embodiments of the present technology.

FIG. 2 is a front view of a sample swab 200 configured in accordance with embodiments of the present technology. The sample swab 200 can be used with the diagnostic device 100 of FIG. 1 and/or any of the other diagnostic devices described herein. The sample swab 200 includes a swab portion 202 coupled to a handle portion 204. The swab portion 202 can include a swab element 206 made of an absorbent material suitable for collecting a sample from a patient, such as polyester, nylon, rayon, cotton, or combinations thereof. The material of the swab element 206 can also be configured for efficient sample elution when the swab element 206 directly contacts a test strip. In some embodiments, for example, the swab element 206 includes a flocked swab material, such as PurFlock or HydraFlock swab material manufactured by Puritan Medical Products (Guildford, Me.). The swab portion 202 can also include an elongate member 208 (e.g., a rod or stick) supporting the swab element 206 and connecting the swab element 206 to the handle portion 204. In some embodiments, the length $L_1$ of the swab portion 202 is relatively short compared to conventional sample swabs in order to limit the insertion depth of the swab portion into the patient's body (e.g., into the nasal cavity). For example, the length $L_1$ can be no more than 0.25 cm, 0.5 cm, 1 cm, 1.5 cm, 1.75 cm, 2 cm, 2.25 cm, 2.5 cm, 2.75 cm, or 3 cm; and/or can be within a range from 2 cm to 3 cm. Optionally, the length $L_1$ can be configured for collecting an anterior nasal sample from the patient. The use of a relatively short swab portion 202 can be advantageous for patient safety and can allow laypersons to perform the sample collection step without supervision from a healthcare professional.

The handle portion 204 is configured to allow the user to hold the sample swab 200. The handle portion 204 can also be configured to limit an insertion depth of the swab portion 202 into the patient's body and/or a diagnostic device (e.g., the device 100 of FIGS. 1A-1G). In the illustrated embodiment, for example, the handle portion includes a narrower neck section 210 coupled to the swab portion 202, and a wider body section 212 extending from the neck section 210. The neck section 210 can have a terminus surface 211 and the wider body portion 212 can have a shoulder 213. In operation, the terminus surface 211 and/or the shoulder 213 can contact a corresponding surface of the diagnostic device (e.g., the upper surface 142 of the device 100 of FIGS. 1A-1G) to position the swab element 206 at a desired position with respect to the test strip, as described further below. The neck section 210 can be beveled, tapered, etc., to be narrower than the body section 212. For example, the neck section 210 can have a diameter or width less than or equal to 0.25 cm, 0.5 cm, 0.75 cm, or 1 cm; and the body section 212 can have a diameter or width greater than 0.5 cm, 0.75 cm, 1 cm, 1.25 cm, or 1.5 cm. In some embodiments, the diameter or width of the body section 212 is greater than the diameter or width of the neck section 210 by at least 1 mm, 2 mm, 3 mm, 4 mm, or 5 mm. In other embodiments, however, the neck section 210 can be omitted and the swab portion 202 can connect directly to the body section 212.

Figure 3:
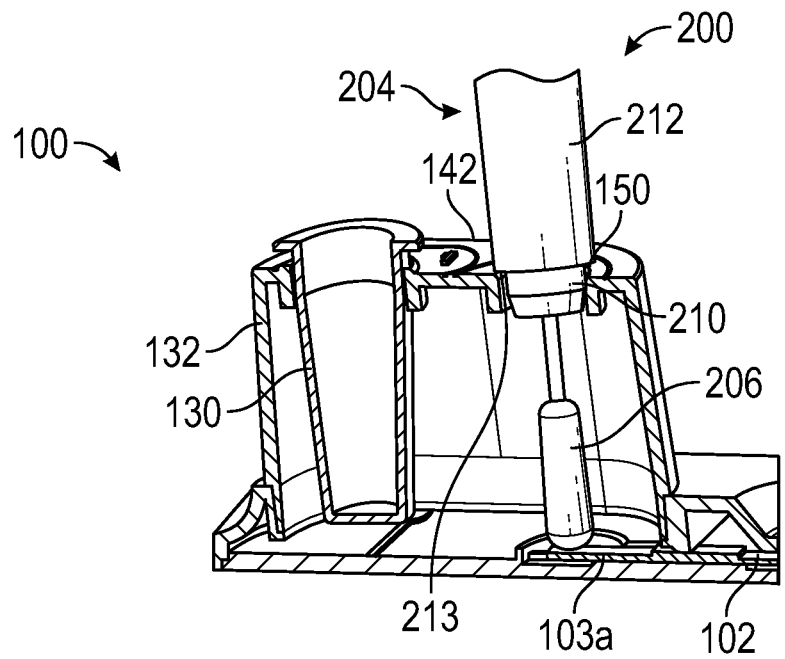
FIG. 3 illustrates the sample swab of FIG. 2 together with the device of FIGS. 1A-1G, in accordance with embodiments of the present technology.

FIG. 3 illustrates the sample swab 200 of FIG. 2 together with the device 100 of FIGS. 1A-1G, in accordance with embodiments of the present technology. The user can insert the sample swab 200 into the aperture 150 of the device 100 until the swab element 206 directly contacts the test strip 102 (e.g., the sample pad portion 103a). As described above, the direct contact between the swab element 206 and the test strip 102 can transfer a fluid sample onto the test strip 102 via capillary action. As shown in FIG. 3, the handle portion 204 can engage the upper surface 142 of the device 100 surrounding the aperture 150 to limit the insertion depth and/or insertion angle of the sample swab 200 into the aperture 150, e.g., so the swab element 206 does not contact the test strip 102 with excessive force. In the illustrated embodiment, for example, the narrower neck section 210 fits into the aperture 150, while the shoulder 213 of the wider body section 212 engages the upper surface 142, thus preventing further downward movement of the sample swab 200 into the device 100. The neck section 212 can be size and shaped to mate with the aperture 150 so that the sample swab 200 is constrained to at least a substantially vertical orientation with the swab element 206 at least substantially perpendicular to the test strip 102.

In some embodiments, the sample swab 200 can be stored in the aperture 150 of the device 100 before use. For example, the handle portion 204 of the sample swab 200 (e.g., the neck section 210) can include retention features (e.g., threading, grooves, etc.) that mate with corresponding retention features on or near the upper surface 142 and/or aperture 150 so the sample swab 200 can be temporarily secured to the device 100. The retention features can be configured to seal the interior of the device 100 and the swab element 206 to maintain sterility. Alternatively or in combination, the device 100 and sample swab 200 can be provided in a unitary package that protects these components from contamination. In other embodiments, however, the swab 200 can be packaged and stored separately from the device 100.

Figure 4:
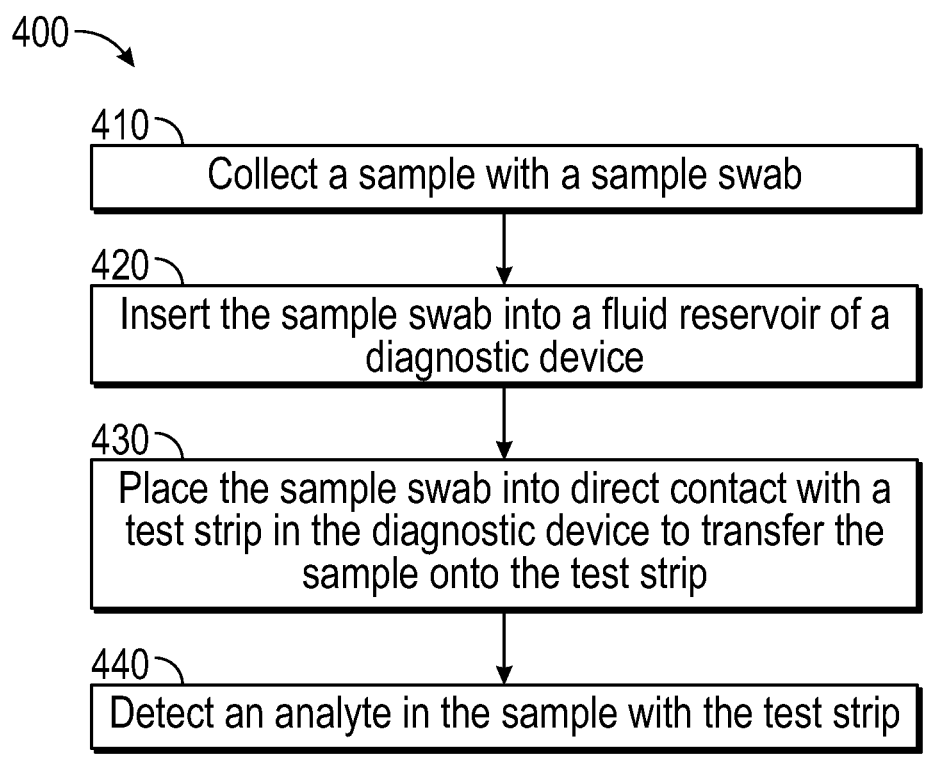
FIG. 4 is a flow diagram illustrating a method for analyzing a sample from a patient, in accordance with embodiments of the present technology.

FIG. 4 is a flow diagram illustrating a method 400 for analyzing a sample from a patient, in accordance with embodiments of the present technology. The method 400 can be performed using any of the devices described herein, such as the diagnostic device 100 of FIGS. 1A-1G and/or the sample swab 200 of FIG. 2. The method 400 begins at step 410 with collecting a sample with a sample swab (e.g., the sample swab 200 of FIG. 2). The sample can be a sample from one or more locations of the patient's body, such as an anterior nasal sample, a buccal sample, oropharyngeal sample, nasopharyngeal sample, etc. The sample can be collected by the patient to be tested, or by another individual.

At step 420, the method 400 includes inserting the sample swab into a fluid reservoir of a diagnostic device (e.g., the fluid reservoir 130 of the device 100 of FIGS. 1A-1G). As previously described, the fluid reservoir can be integrated into a housing of the diagnostic device. The fluid reservoir can contain a solution for hydrating the sample swab, lysing or otherwise interacting with a sample on the swab, etc. In some embodiments, step 420 includes immersing the sample swab in the solution for a particular period of time, e.g., no more than 1 second, 5 seconds, 10 seconds, or 30 seconds.

At step 430, the method 400 continues with placing the sample swab into direct contact with a test strip in the diagnostic device to transfer the sample onto the test strip. As previously described, the test strip can be contained within the same diagnostic device as the fluid reservoir (e.g., the device 100 of FIG. 1). For example, the diagnostic device can include an aperture (e.g., aperture 150 of the device 100 of FIG. 1) that exposes a portion of the test strip for access by the sample swab. The sample swab can be placed into direct contact with the test strip so the hydrated sample on the sample swab is eluted onto the test strip, e.g., via capillary action. The contact between the sample swab and the test strip can be maintained for a suitable period of time, e.g., no more than 1 second, 5 seconds, 10 seconds, or 30 seconds.

As described above, the diagnostic device can include at least one guide structure configured to position the sample swab at a desired position with respect to the test strip, such as at an appropriate insertion angle (e.g., at least a substantially vertical orientation) and/or insertion depth (e.g., a depth that provides a desired spacing or contact force against the test strip). The guide structure can be, for example, a stop surface (e.g., the upper surface 142 of the device 100 of FIGS. 1A-1G) at least partially surrounding an aperture (e.g., the aperture 150 of the device 100 of FIGS. 1A-1G) for receiving the sample swab. Optionally, the guide structure can control the insertion depth and/or insertion angle by engaging a handle portion or other portion of the sample swab.

At step 440, the method 400 includes detecting an analyte in the sample with the test strip. The test strip can include one or more reagents (e.g., capture antibodies, detection antibodies, secondary antibodies, etc.) that collectively interact with the analyte to generate a detectable (e.g., visible) indication, in accordance with LFA techniques known to those of skill in the art. For example, the test strip can include at least one reagent configured to detect SARS-CoV-2 virus, or an antigen thereof (e.g., a nucleocapsid antigen), as described in greater detail below.

Figure 5A:
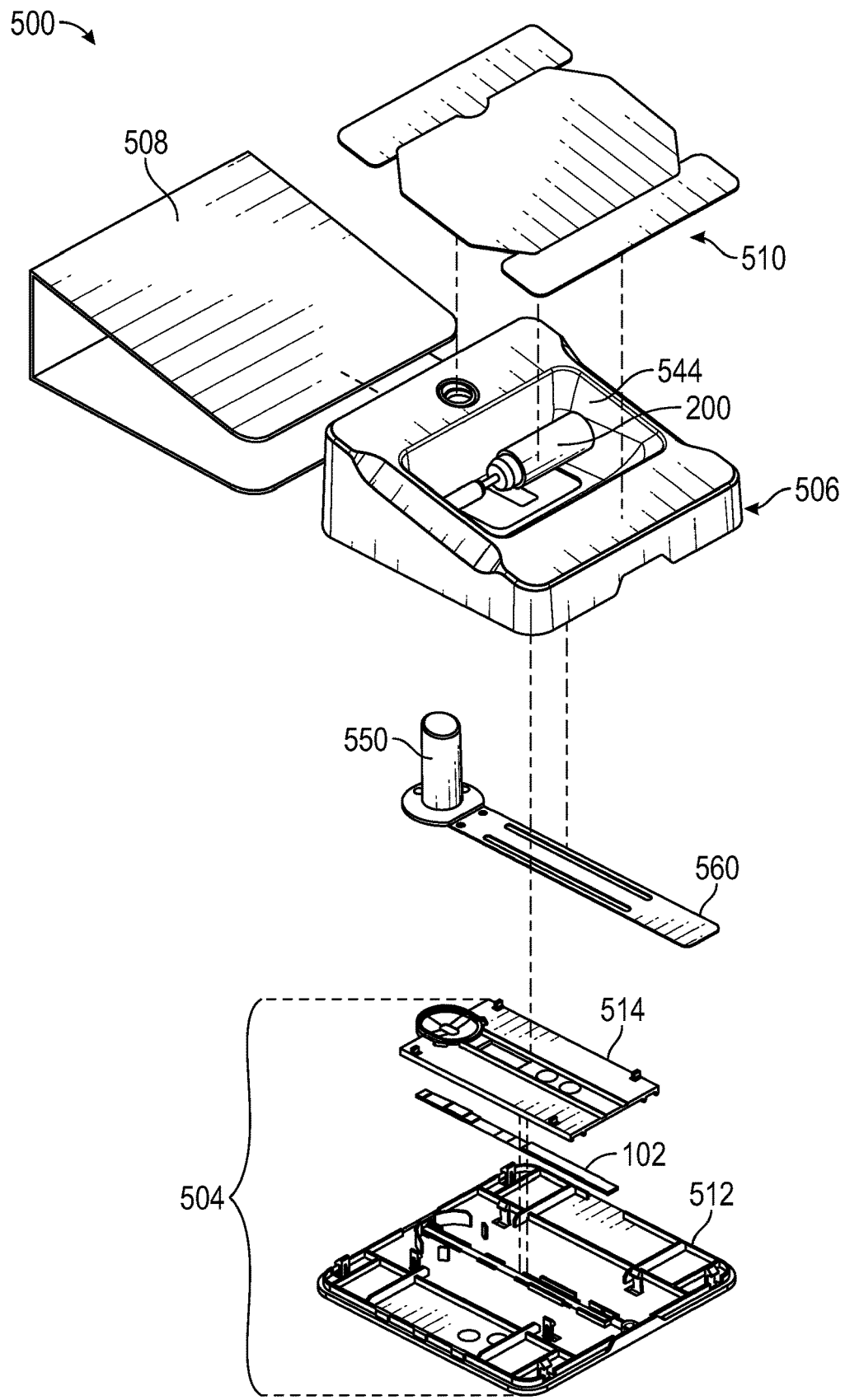
FIG. 5A is an exploded view of another diagnostic device for analyzing a patient sample configured in accordance with embodiments of the present technology.

FIGS. 5A-5O illustrate a diagnostic device 500 ("device 500") for analyzing a patient sample configured in accordance with embodiments of the present technology. Specifically, FIG. 5A is an exploded view of the device 500, FIG. 5B is a perspective view of the device, FIGS. 5C-5H are various views of components of the device 500, and FIGS. 5I-5O illustrate a process for operating the device 500.

Referring first to FIG. 5A, the device 500 can be a test cassette, cartridge, or similar structure for housing a test strip 102. In some embodiments, the device 500 is configured to receive a patient sample from a sample swab (e.g., sample swab 200) and detect at least one analyte (e.g., SARS-CoV-2 virus or a component thereof) in the sample via the test strip 102. As described in detail below, the device 500 can be simpler to operate and can require fewer components than devices that receive sample droplets from a dropper bottle, pipette, etc. The device 500 includes a housing configured to partially or fully enclose the test strip 102. The housing can include a housing base 504 configured to receive the test strip 102, and a housing cover 506 configured to couple to the housing base 504 to enclose the test strip 102. The device 500 can optionally include various components for packaging the housing base 504 and housing cover 506, such as a packaging cover 508 and/or a plurality of sealing labels 510.

Figure 5B:
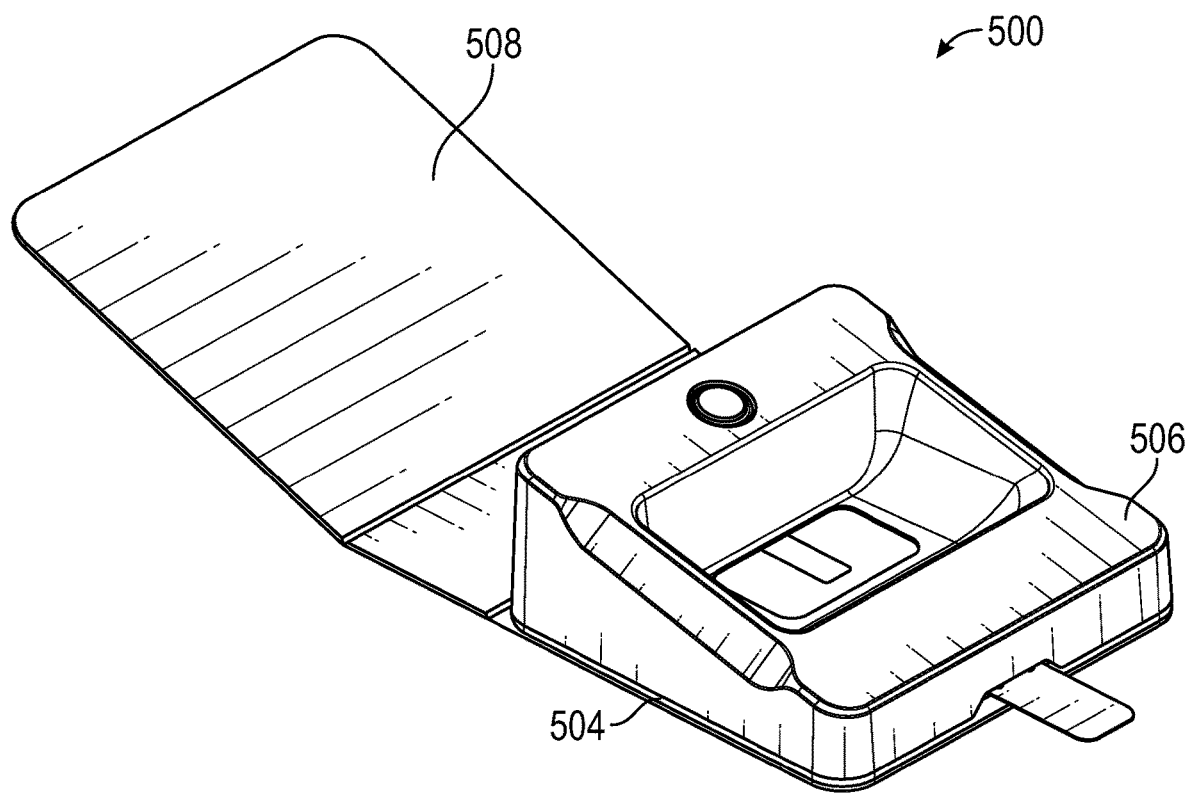
FIG. 5B is a perspective view of the device of FIG. 5A.

Referring next to FIG. 5B, when the device 500 is assembled, the housing base 504 forms the lower portion of the device 500 and the housing cover 506 forms the upper portion of the device 500. The housing base 504 and housing cover 506 can be made of any suitable material (e.g., plastic), and can be transparent, translucent, or opaque, as desired. The features of the housing base 504 and housing cover 506 are described in greater detail below with reference to FIGS. 5C-5H.

The packaging cover 508 can be coupled to the housing base 504. The packaging cover 508 can be configured to partially or fully enclose the housing base 504 and housing cover 506 to protect these components, e.g., during shipping and/or storage. For example, the packaging cover 508 can include a set of panels or sheets that can be folded over the housing cover 506 (FIG. 5B shows the packaging cover 508 in an unfolded configuration; FIG. 5A shows the packaging cover 508 in a folded configuration). In other embodiments, the packaging cover 508 is optional and can be omitted.

Figure 5C:
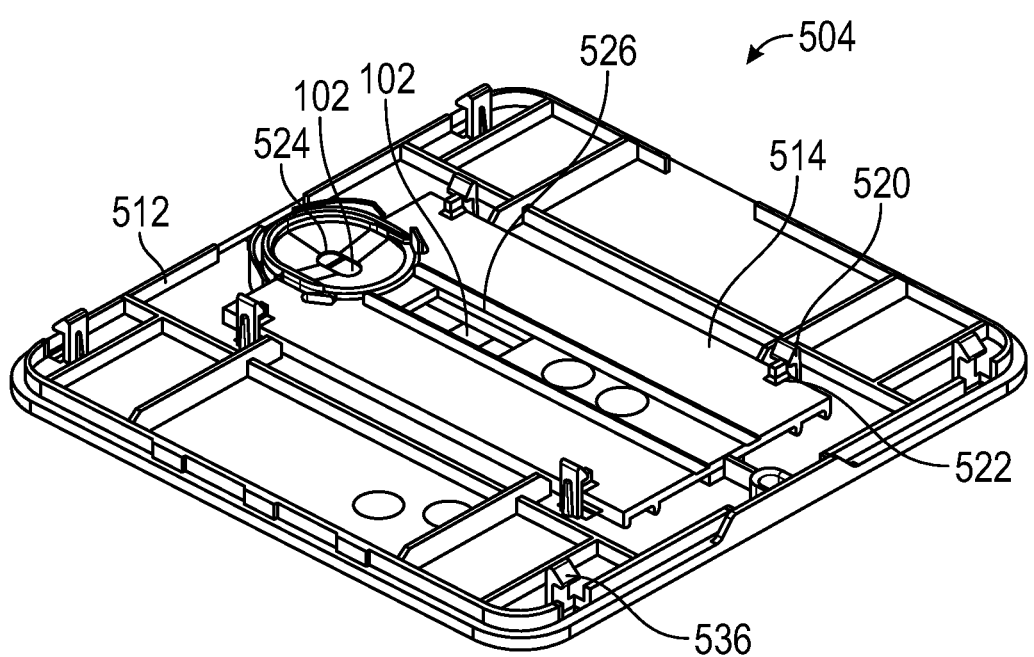
FIG. 5C is a perspective view of a housing base of the device of FIG. 5A.
Figure 5D:
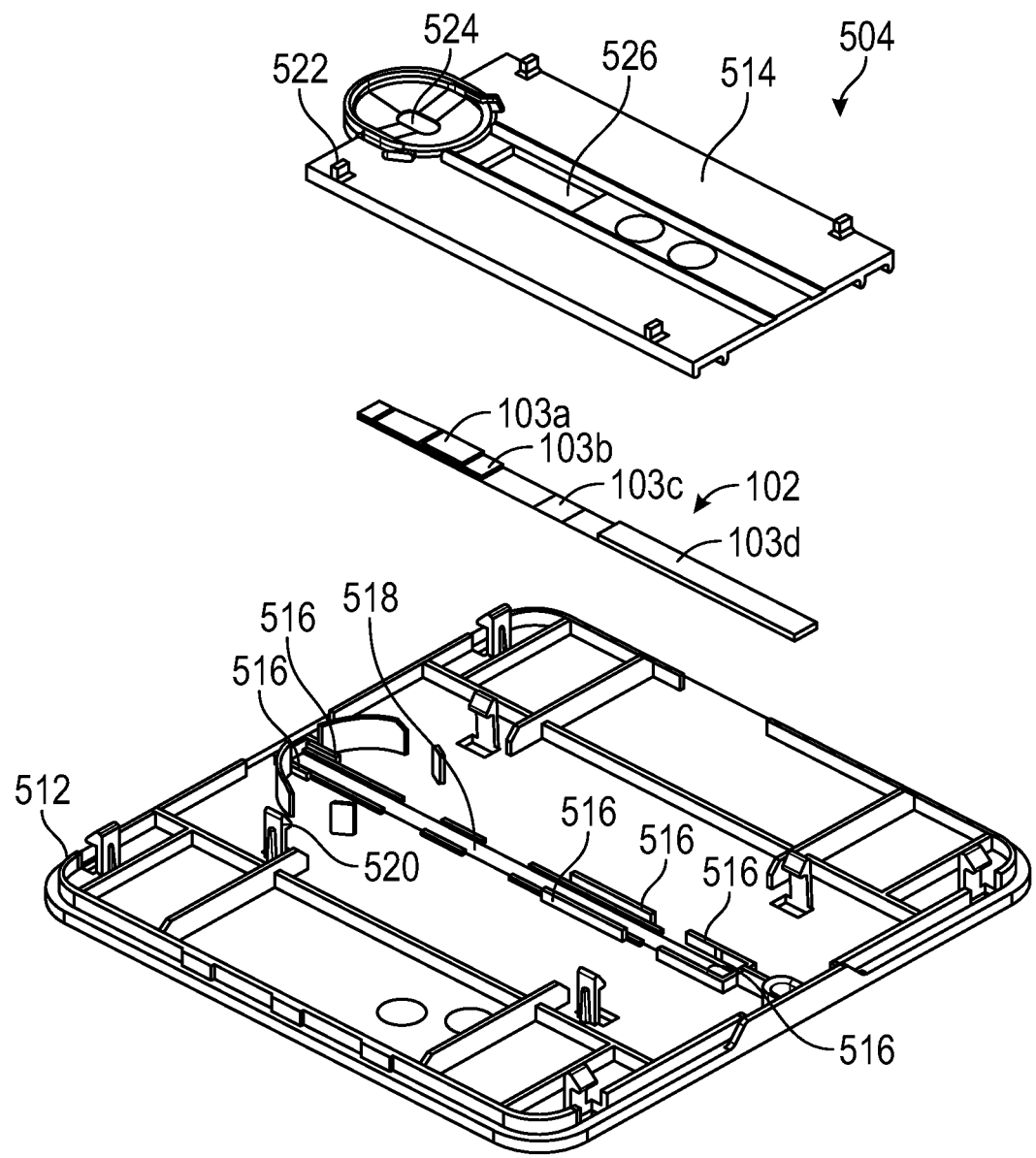
FIG. 5D is an exploded view of the housing base of FIG. 5C.

FIGS. 5C and 5D are perspective and exploded views of the housing base 504. The housing base 504 can have a generally flattened shape, such as a square shape, rectangular shape, or any other suitable shape. The housing base 504 can include various structures for supporting and/or retaining the test strip 102. In the illustrated embodiment, for example, the housing base 504 includes a base plate 512 configured to support the test strip 102, and a cover plate 514 configured to couple to the base plate 512 to retain and compress the test strip 102 against the base plate 512. As best seen in FIG. 5D, the base plate 512 can include a set of walls 516 (e.g., discontinuous or continuous walls) defining an elongate channel 518 for receiving the test strip 102. The elongate channel 518 have a similar geometry as the test strip (e.g., with respect to length and/or width). Optionally, the walls 516 can include one or more protrusions (omitted in FIG. 5D for simplicity) that engage (e.g., compress) the test strip 102 to secure the test strip 102 within the elongate channel 518. The protrusions can be identical or similar to the protrusions 112 of the device 100 of FIGS. 1A-1G, and can be at any suitable location along the elongate channel 518, such as at or near the ends of the elongate channel 518, at or near the central section of the elongate channel 518, and/or combinations thereof.

The cover plate 514 can be coupled to the base plate 512 so that the test strip 102 is between the base plate 512 and the cover plate 514. The cover plate 514 and base plate 512 can be coupled using any suitable technique, such as interference fit, snap fit, adhesives, bonding, fasteners, and the like. In the illustrated embodiment, for example, the base plate 512 includes a set of hooks 520, and the cover plate 514 includes a corresponding set of protrusions 522. Each hook 520 engages with a corresponding protrusion 522 to connect the base plate 512 to the cover plate 514. Although the illustrated embodiment includes four hooks 520 and protrusions 522, in other embodiments, the base plate 512 and cover plate 514 can include fewer or more hooks 520 and protrusions 522, respectively.

When coupled to the base plate 512, the cover plate 514 can partially or fully cover the test strip 102. The cover plate 514 and the base plate 512 can apply pressure to the test strip 102 to constrain the test strip 102 and/or enhance fluid flow through the test strip 102. In some embodiments, the cover plate 514 includes one or more openings or windows to expose portions of the test strip 102. For example, the cover plate 514 can include a first opening 524 exposing a sample pad portion 103a of the test strip 102 to allow sample transfer onto the test strip 102, as described in greater detail below. The cover plate 514 can also include a second opening 526 exposing a readout portion 103c of the test strip 102 so a user can view the test results.

Figure 5E:
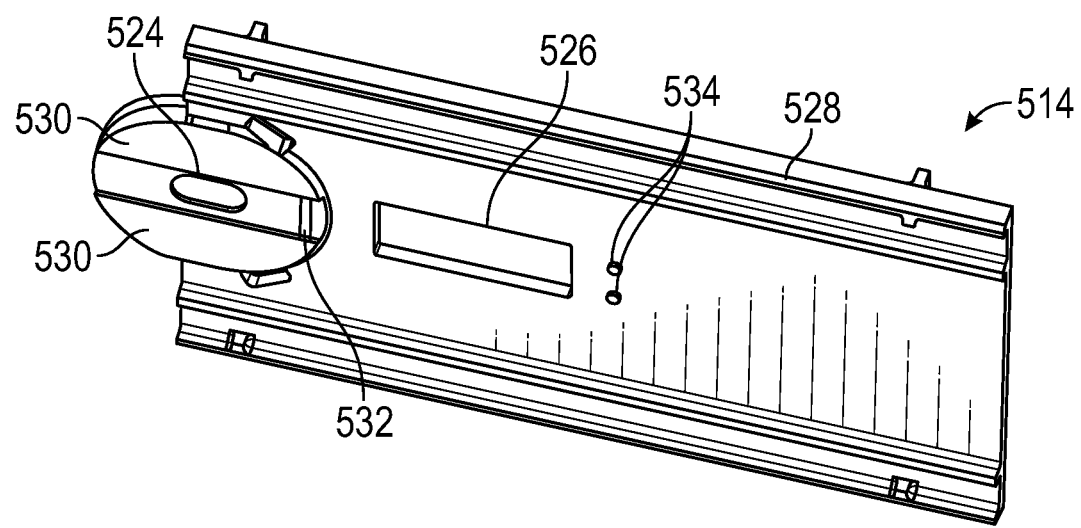
FIG. 5E is a bottom perspective view of a cover plate of the housing base of FIG. 5C.

FIG. 5E is a bottom perspective view of the cover plate 514. In some embodiments, the cover plate 514 includes a bottom surface 528 having structures that contact the test strip 102. In the illustrated embodiment, for example, the bottom surface 528 includes a set of flattened surfaces 530 and a strut 532 near the first opening 524, and a pair of protrusions 534 near the second opening 526. The flattened surfaces 530, strut 532, and protrusions 534 can apply pressure to different portions of the test strip 102 to further secure the test strip 102 and/or enhance fluid flow through the test strip 102. For example, the flattened surfaces 530 can contact the sample pad portion 103a of the test strip 102, the strut 532 can contact the conjugate pad portion 103b of the test strip 102, and the protrusions 534 can contact a wicking pad portion 103d of the test strip 102. In other embodiments, however, the number, arrangement, and/or geometries of the flattened surface 530, strut 532, and/or protrusions 534 can be varied as desired. Moreover, in other embodiments, one or more of the flattened surfaces 530, strut 532, and/or protrusions 534 can be omitted.

FIGS. 5F and 5G are perspective and exploded views of the housing cover 506, respectively. The housing cover 506 is configured to couple to the housing base 504 to enclose and protect the test strip 102. The housing cover 506 and housing base 504 can be coupled using any suitable technique, such as interference fit, snap fit, adhesives, bonding, fasteners, and the like. For example, referring again to FIG. 5C, the base plate 512 of the housing base 504 can include a set of hooks 536 that couple to corresponding protrusions on the underside of the housing cover 506 (not shown in FIGS. 5F and 5G).

As shown in FIGS. 5F and 5G, the housing cover 506 is a raised structure having a front portion 540a, a back portion 540b, and an upper surface 542. In the illustrated embodiment, the height $H_3$ of the back portion 540b is greater than the height $H_4$ of the front portion 540a such that the upper surface 542 is angled or sloped. The height $H_3$ of the back portion 540b can be at least 2 cm, 2.5 cm, 3 cm, 3.5 cm, 4 cm, 4.5 cm, 5 cm, 5.5 cm, or 6 cm; and/or within a range from 3 cm to 6 cm. The height $H_4$ of the front portion 540a can be no more than 0.5 cm, 1 cm, 1.5 cm, 2 cm, 2.5 cm, 3 cm, 3.5 cm, or 4 cm; and/or within a range from 0.5 cm to 2.5 cm. In other embodiments, however, the height $H_3$ can be similar or equal to the height $H_4$.

In some embodiments, the housing cover 506 includes a recess 544 in the upper surface 542, and a window 546 at the bottom of the recess 544 for viewing a readout portion of the test strip 102. The window 546 can be a flattened structure made of a transparent or translucent material to expose the test strip 102 so the user can view the results of the testing procedure. The window 546 can optionally be or include a lens having a magnification to enhance readability of the results. The recess 544 can be sufficiently deep so the window 546 is adjacent to or near the test strip 102 (e.g., the readout portion 103c (FIG. 5D)). For example, the depth $D_1$ of the recess 544 can be at least 1 cm, 1.5 cm, 2 cm, 2.5 cm, 3 cm, 3.5 cm, 4 cm, 4.5 cm, or 5 cm; and/or within a range from 2 cm to 4 cm. Optionally, as shown in FIG. 5A, the recess 544 can also be configured to store the sample swab 200, e.g., during shipment and/or storage of the device 500.

Referring to FIG. 5G, the housing cover 506 can include a fluid reservoir 550 (e.g., a tube, vial, chamber, etc.) configured to hold a solution (e.g., a buffer solution, reagent solution, lysing solution, wash solution, etc.). The solution can be identical or similar to the solution previously described with reference to the device 100 of FIGS. 1A-1G. For example, the solution can be used to hydrate the sample swab, elute a sample from the sample swab, lyse the sample, react with the sample, etc. The fluid reservoir 550 can be configured to hold any suitable volume of solution, such as at least 50 µL, 75 µL, 100 µL, 200 µL, 300 µL, 400 µL, 500 µL, 600 µL, 700 µL, 800 µL, 900 µL, or 1 mL.

The fluid reservoir 550 can be integrated with or otherwise connected to the housing cover 506 such that the fluid reservoir 550 cannot be separated from the housing cover 506 without destroying the device 500. In the illustrated embodiment, for example, the fluid reservoir 550 is a separate component (e.g., a tube or vial) that fits within an opening 552 in the upper surface 542 of the housing cover 506. The fluid reservoir 550 can be permanently affixed to the housing cover 506 during the manufacturing process (e.g., by bonding, adhesives, interference fit, snap fit, etc.). In other embodiments, however, the fluid reservoir 550 can be integrally formed with the housing cover 506 as a single unitary component. The fluid reservoir 550 can be at the back portion 540b of the housing cover 506, the front portion 540a, or any other suitable location.

The fluid reservoir 550 includes a first aperture 554 at an upper portion of the fluid reservoir 550, which can be configured to allow the sample swab to access the fluid reservoir 550. The first aperture 554 can have any suitable geometry, such as circular, oval, square, rectangular, or any other suitable shape. In some embodiments, the first aperture 554 has a diameter or width less than or equal to 0.25 cm, 0.5 cm, 0.75 cm, 1 cm, or 1.5 cm. Optionally, before use, the first aperture 554 can be covered with a cap 556 or other sealing element to contain the solution and/or maintain sterility.

The fluid reservoir 550 can include a second aperture 558 at a bottom portion of the fluid reservoir 550. The second aperture 558 can allow the eluted sample to flow downward out of the fluid reservoir 550 and onto the test strip 102, as described in greater detail below with reference to FIGS. 5H and 5I. The second aperture 558 can be circular, oval, square, rectangular, or any other suitable geometry. In some embodiments, the second aperture 558 has a diameter or width less than or equal to 0.25 cm, 0.5 cm, 0.75 cm, 1 cm, or 1.5 cm.

The second aperture 558 can initially be covered by a sealing element 560 (e.g., a foil strip) so that the solution is retained within the fluid reservoir 550. The sealing element 560 can have an elongate, generally linear shape including a first end 562a coupled to the fluid reservoir 550 and a second end 562b spaced apart from the fluid reservoir 550. The first end 562a can be temporarily coupled to the second aperture 558 to seal the solution within the fluid reservoir 550. The second end 562b can be configured as a pull tab or similar structure so the user can manually remove the sealing element 560 from the fluid reservoir 550, as described further below. The sealing element 560 can be sufficiently long so that when the housing cover 506 is assembled, the second end 562a protrudes outward from the front portion 540a of the housing cover 506 (e.g., from slot 564 in the front portion 540a). For example, the length $L_2$ of the sealing element 560 can be at least 5 cm, 6 cm, 7 cm, 8 cm, 9 cm, 10 cm, 11 cm, 12 cm, 13 cm, 14 cm, or 15 cm.

Figure 5H:
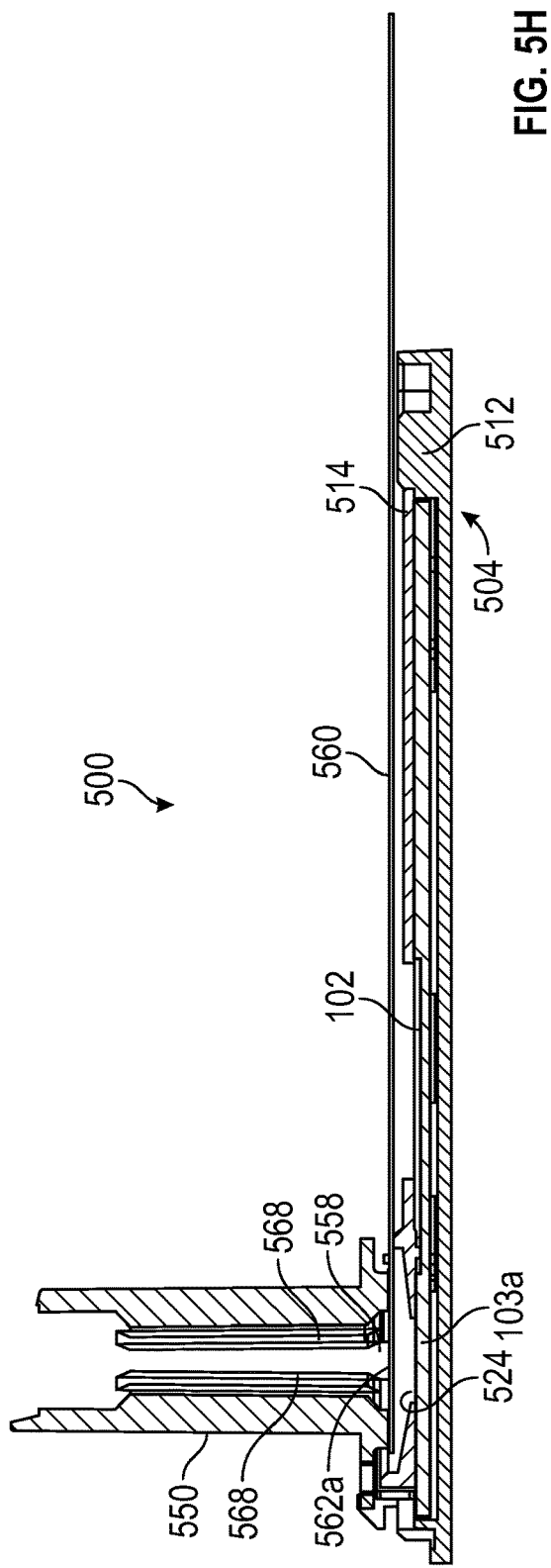
FIG. 5H is a cutaway side cross-sectional view of the device of FIG. 5A.

FIG. 5H is a cutaway side cross-sectional view of the device 500 showing the arrangement of the test strip 102, fluid reservoir 550, and sealing element 560. As previously described, when the device 500 is assembled, the test strip 102 can be retained between the base plate 512 and cover plate 514 of the housing base 504, with a portion of the test strip 102 (e.g., the sample pad portion 103a) exposed via the second opening 524 in the cover plate 514. The portions of the cover plate 514 surrounding the second opening 524 can optionally have a sloped, funnel-like shape to direct fluid onto the exposed portion of the test strip 102. In other embodiments, however, the portions of the cover plate 514 surrounding the second opening 524 can be flush with the second opening 524 or otherwise substantially planar.

The fluid reservoir 550 can be above the test strip 102, so that the second aperture 558 of the fluid reservoir 550 is directly above and/or aligned with the second opening 524 of the cover plate 514. This arrangement can allow fluid to flow from the fluid reservoir 550 onto the test strip 102 via the second aperture 558 and second opening 524. Before the device 500 is used, the second aperture 558 can be sealed by the first end 562a of the sealing element 560. As shown in FIG. 5H, the second end 562a of the sealing element 560 can be positioned between the second aperture 558 of the fluid reservoir 550 and the test strip 102.

Figure 5I:
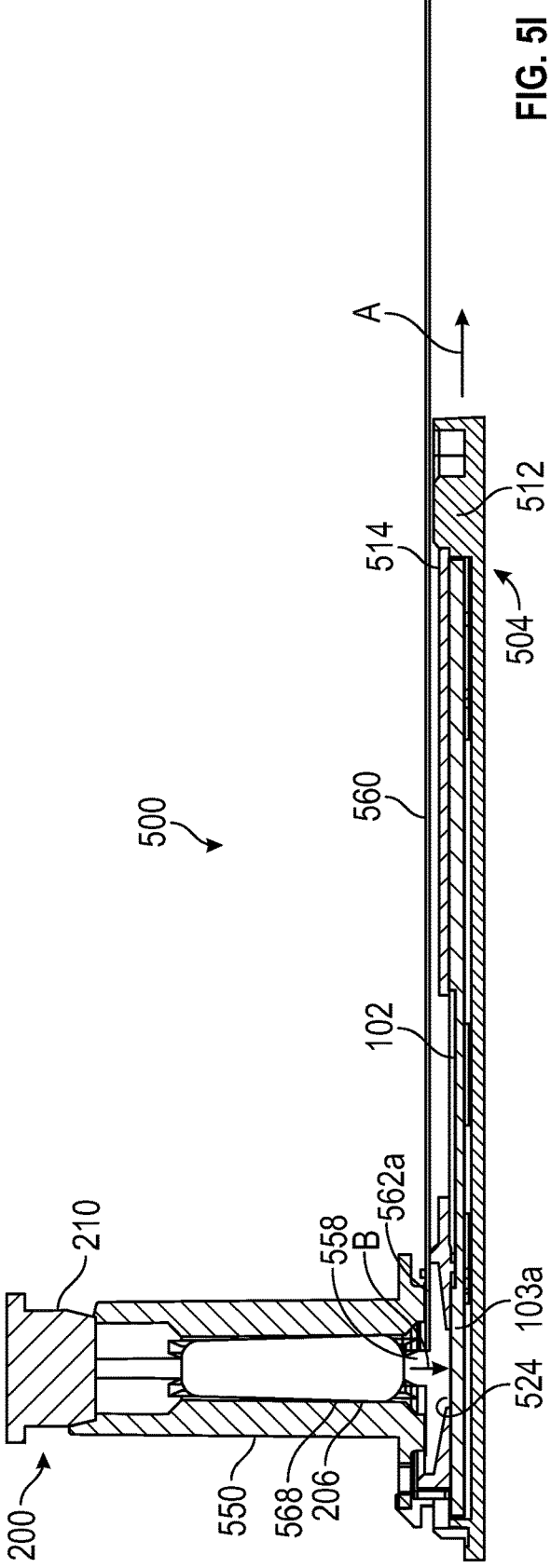
FIG. 5I is a cutaway side cross-sectional view of the device of FIG. 5A together with the sample swab of FIG. 2.

FIG. 5I is a cutaway side cross-sectional view of the device 500 showing a sample swab 200 inserted into the fluid reservoir 550. As previously discussed, the fluid reservoir 550 can contain a solution for eluting the sample from the sample swab 200. Optionally, the fluid reservoir 550 can include at least one extraction structure configured to contact and/or compress the sample swab 200 to enhance sample elution. For example, the extraction structure can include a plurality of elongate, vertical ribs 568 (FIG. 5H) configured to press against the swab element 206 to squeeze fluid (e.g., the hydrated sample) from the swab element 206. Alternatively or in combination, the extraction structure can include other elements, such as horizontal ribs, angled ribs, spiral or helical ribs, protrusions, texturing, and/or suitable combinations thereof.

Optionally, the fluid reservoir 550 can be configured to control the insertion depth and/or insertion angle of the sample swab 200. For example, the fluid reservoir 550 can engage a portion of the sample swab 200 to constrain the sample swab 200 to a vertical or substantially vertical orientation, which may further enhance sample elution. Additionally, the engagement between the fluid reservoir 550 and sample swab 200 can prevent the sample swab 200 from being inserted too deep into the fluid reservoir 550, which could damage the sample swab 200 and/or penetrate the sealing element 560. In the illustrated embodiment, for example, the walls of the fluid reservoir 550 engage the swab element 206 and the neck section 210 to constrain the sample swab 200 to the appropriate insertion depth and/or angle. Alternatively or in combination, the device 500 can include other features for controlling insertion depth and/or angle, such as a stop surface or other guide structure on the housing cover 506 near the fluid reservoir 550 (e.g., similar to the embodiments described with reference to the device 100 of FIGS. 1A-1G).

Once the sample has been eluted from the sample swab 200 and into the solution in the fluid reservoir 550, the sealing element 560 can be removed from the fluid reservoir 550, e.g., by pulling or otherwise displacing the sealing element 560 along direction A. The removal of the sealing element 560 can partially or fully uncover the second aperture 558, thus allowing eluted sample to flow downward out of the fluid reservoir 550, through the second opening 524 in the cover plate 514, and onto the test strip 102. The sample swab 200 can remain in the fluid reservoir 550 during this process, or can be removed from the fluid reservoir 550 before the second aperture 558 is uncovered.

In the embodiments of FIG. 5I, the swab element 206 of the sample swab 200 is spaced apart from and does not directly contact the test strip 102, even after the sealing element 560 has been removed. For example, the second aperture 558 of the fluid reservoir 550 can be vertically spaced apart from the second opening 524 of the cover plate 514 by at least 0.1 mm, 0.5 mm, 1 mm, 1.5 mm, 2 mm, 2.5 mm, 3 mm, or more. In such embodiments, sample transfer onto the test strip 102 can occur primarily due to fluid flow out of the fluid reservoir 550.

In other embodiments, however, the device 500 can be configured such that the swab element 206 directly contacts the test strip 102 after removal of the sealing element 560. Accordingly, when the sealing element 560 is removed from the second aperture 558, the sample can be transferred onto the test strip 102 by the direct contact between the swab element 206 and the test strip 102. Additionally, the sample eluted into the solution in the fluid reservoir 550 can flow around the swab element 206 and onto the test strip 102, which can be helpful to further enhance the efficacy of sample transfer onto the test strip 102. In some embodiments, there is little or no vertical separation between the second aperture 558 of the fluid reservoir 550 and the second opening 524 of the cover plate 514 (e.g., the vertical separation distance can be less than 2 mm, 1.5 mm, 1 mm, 0.5 mm, or 0.1 mm). Alternatively or in combination, the device 500 can include a mechanism for bringing the test strip 102 into direct contact with the sample swab 200 after the sealing element 560 is removed. For example, the device 500 can include a spring, expandable material, flap, and/or other movable components configured to elevate a portion of the test strip 102 (e.g., the sample pad portion 103*a*) so the test strip 102 contacts the swab element 206. The device 500 can further include a guide structure (e.g., a stop surface or similar feature in or near the fluid reservoir 550) for controlling the insertion depth and/or insertion angle of the sample swab 200 when the swab element 206 directly contacts the test strip 102, as previously discussed.

Figure 5J:
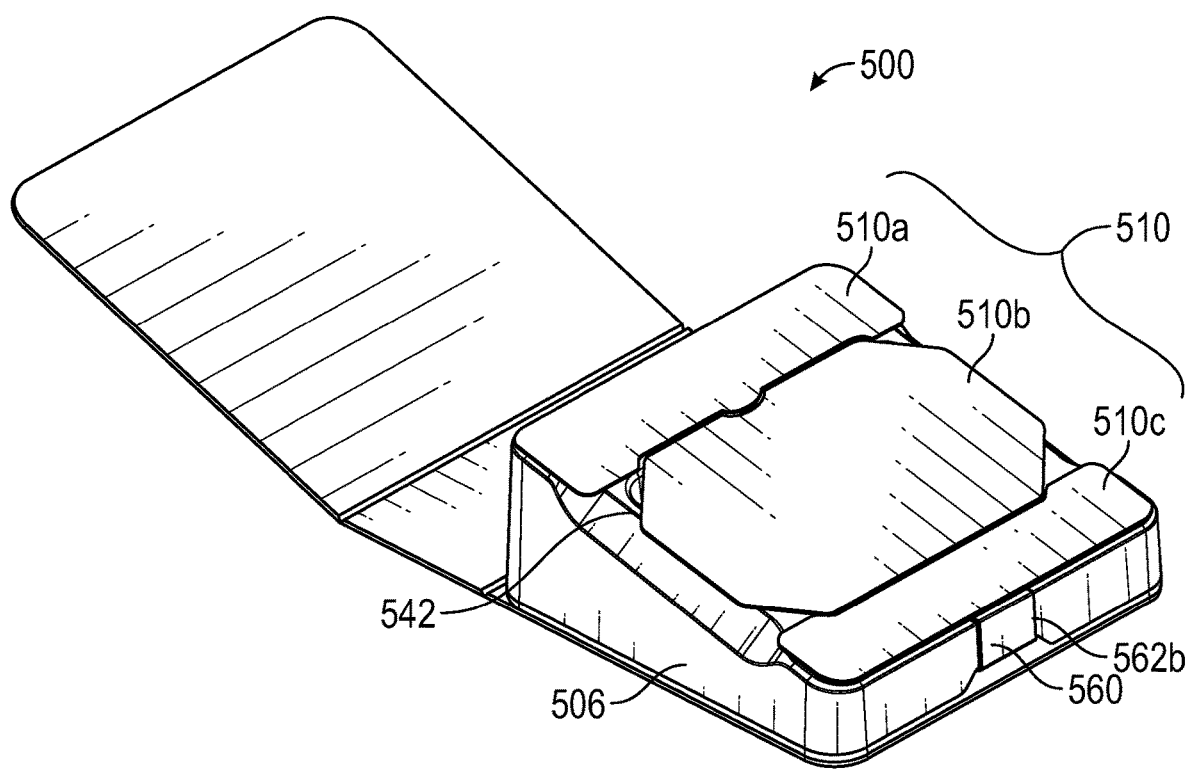

FIGS. 5J-5O illustrate a process for operating the device 500. Referring first to FIG. 5J, the device 500 can be stored and/or shipped with a plurality of sealing labels 510 (e.g., adhesive sheets or stickers) partially or entirely covering the upper surface 542 of the housing cover 506. In the illustrated embodiment, the sealing labels 510 include a first sealing label 510*a* covering the fluid reservoir 550, a second sealing label 510*b* covering the recess 544, and a third sealing label 510*c* attaching the second end 562*b* of the sealing element 560 to the housing cover 506. The sealing labels 510 can optionally include instructions, markings, etc., indicating the order in which the sealing labels 510 should be removed (e.g., the first sealing label 510*a* is labeled with a "1," the second sealing label 510*b* is labeled with a "2," and the third sealing label 510*c* is labeled with a "3."). In other embodiments, however, the number and/or arrangement of the sealing labels 510 can be varied as desired. For example, one or more of the sealing labels 510 can be combined into a single sealing label, separated into discrete sealing labels, and/or omitted.

Figure 5K:
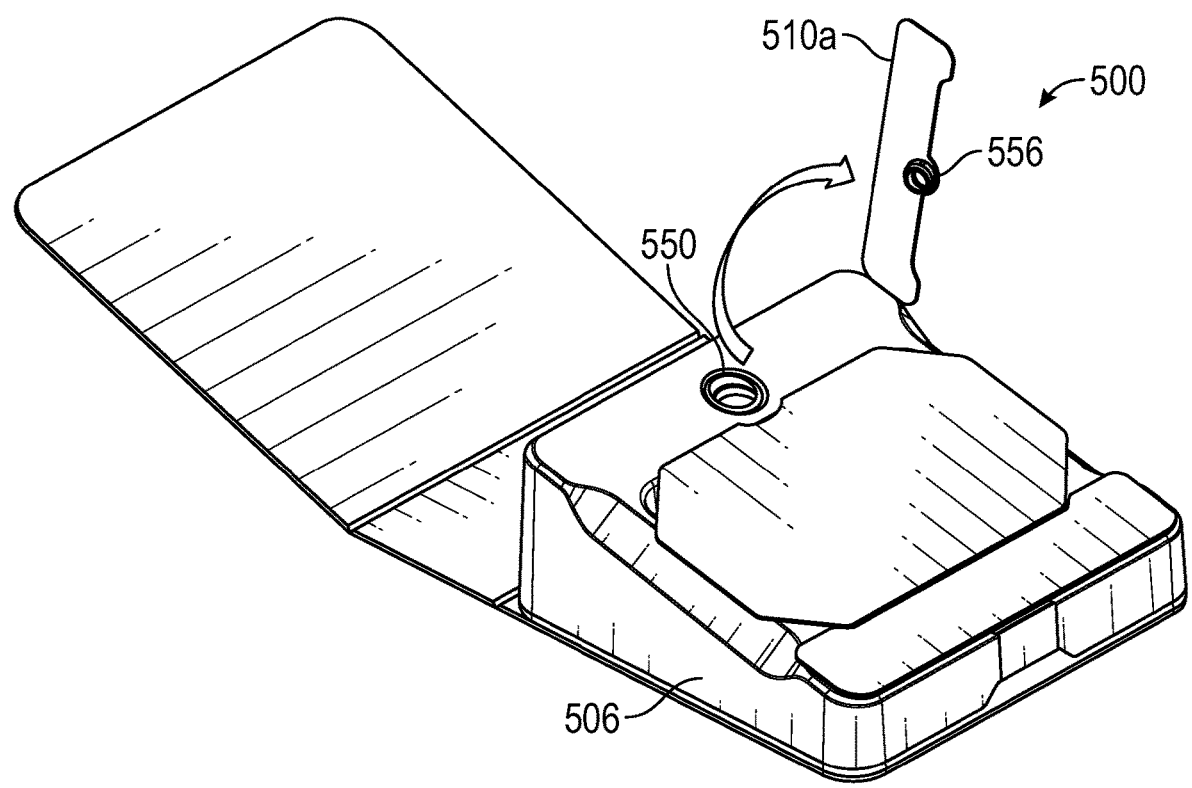

Referring next to FIG. 5K, in an initial stage of operating the device 500, the user can remove the first sealing label 510*a* to expose the fluid reservoir 550 in the housing cover 506. Optionally, the first sealing label 510*a* can be coupled to the cap 556 of the fluid reservoir 550 so that the cap 556 is removed along with the first sealing label 510*a*. Alternatively, the cap 556 can be removed after the first sealing label 510*a* is removed, or can be omitted from the device 500 altogether.

Figure 5L:
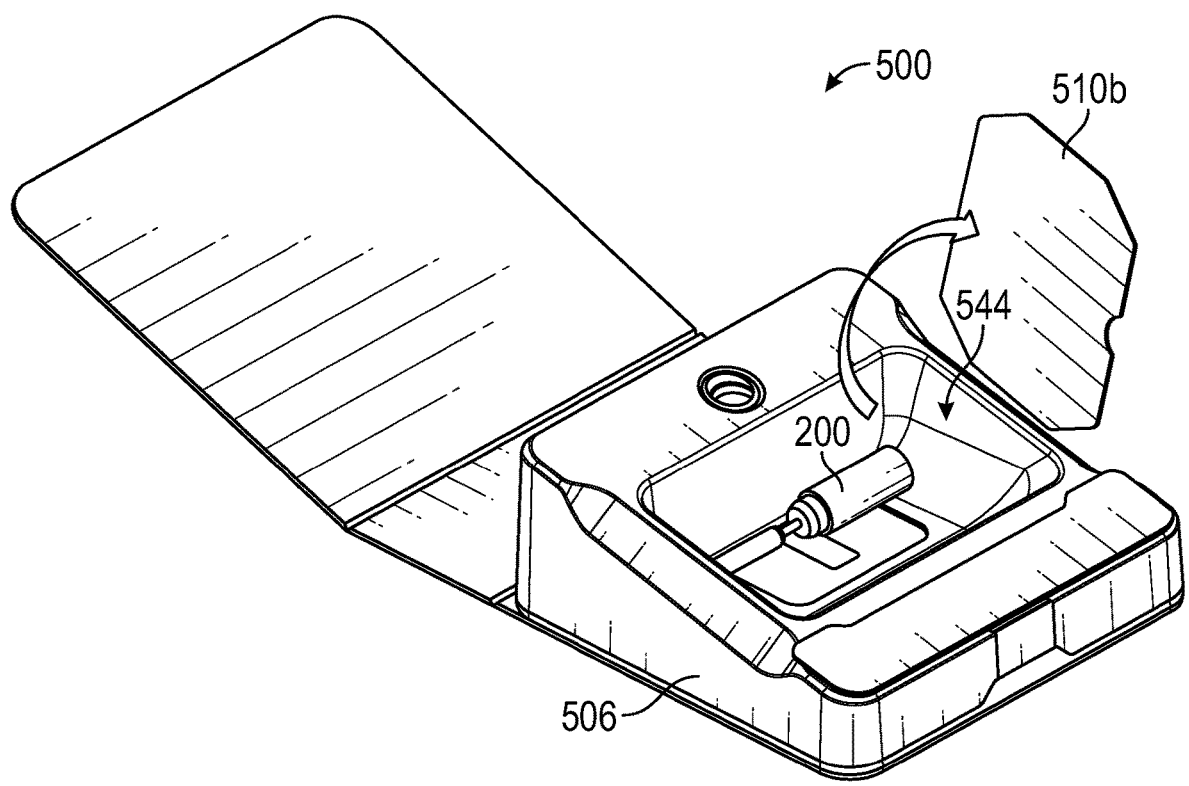

Referring next to FIG. 5L, the user can then remove the second sealing label 510*b* to expose the recess 544 in the housing cover 506. As previously described, the recess 544 can be used to store the sample swab 200. Alternatively, the sample swab 200 can be provided separately from the device 500. The sample swab 200 can be provided in a sterile package (omitted for clarity). The user can then use the sample swab 200 to collect a patient sample (e.g., an anterior nasal sample).

Figure 5M:
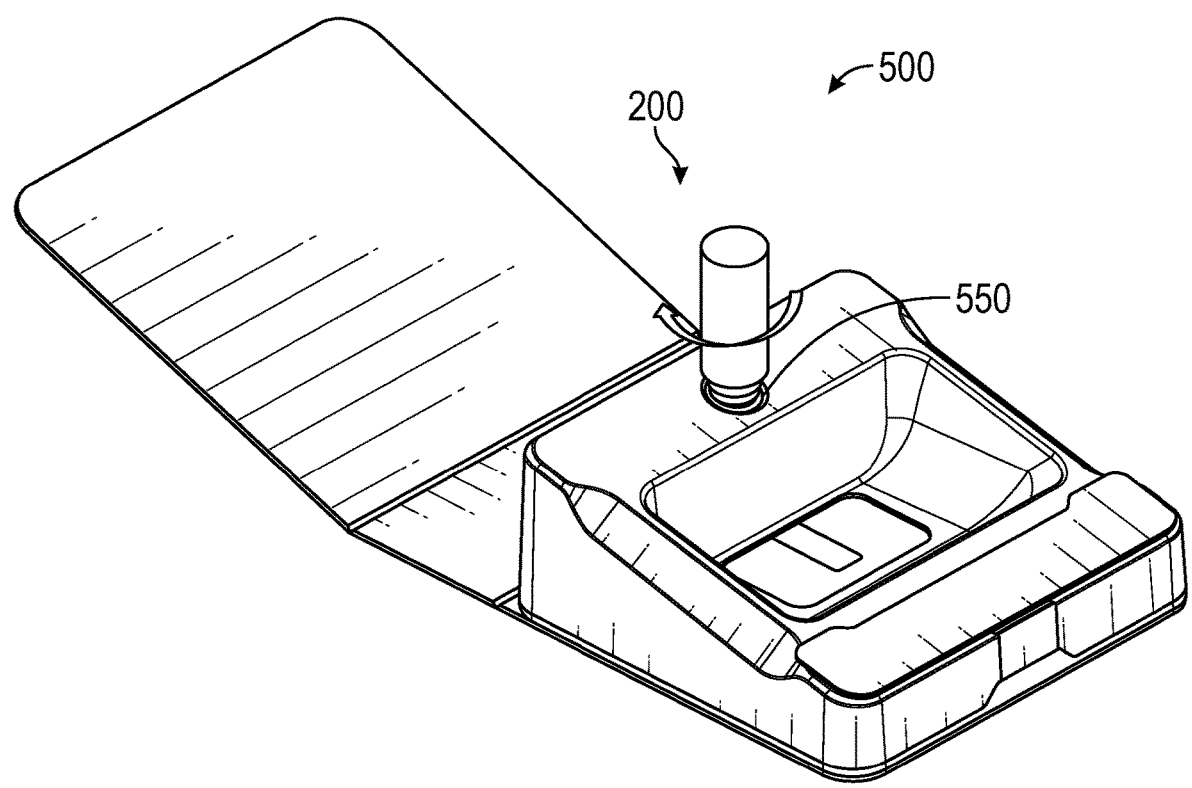

Referring next to FIG. 5M, the user can then insert the sample swab 200 into the fluid reservoir 550 to elute the collected sample into the solution in the fluid reservoir 550. Optionally, the user can rotate or otherwise move the sample swab 200 within the fluid reservoir 550 to facilitate sample elution, e.g., by pressing the sample swab against extraction structures within the fluid reservoir 550 to squeeze fluid out of the sample swab 200.

Figure 5N:
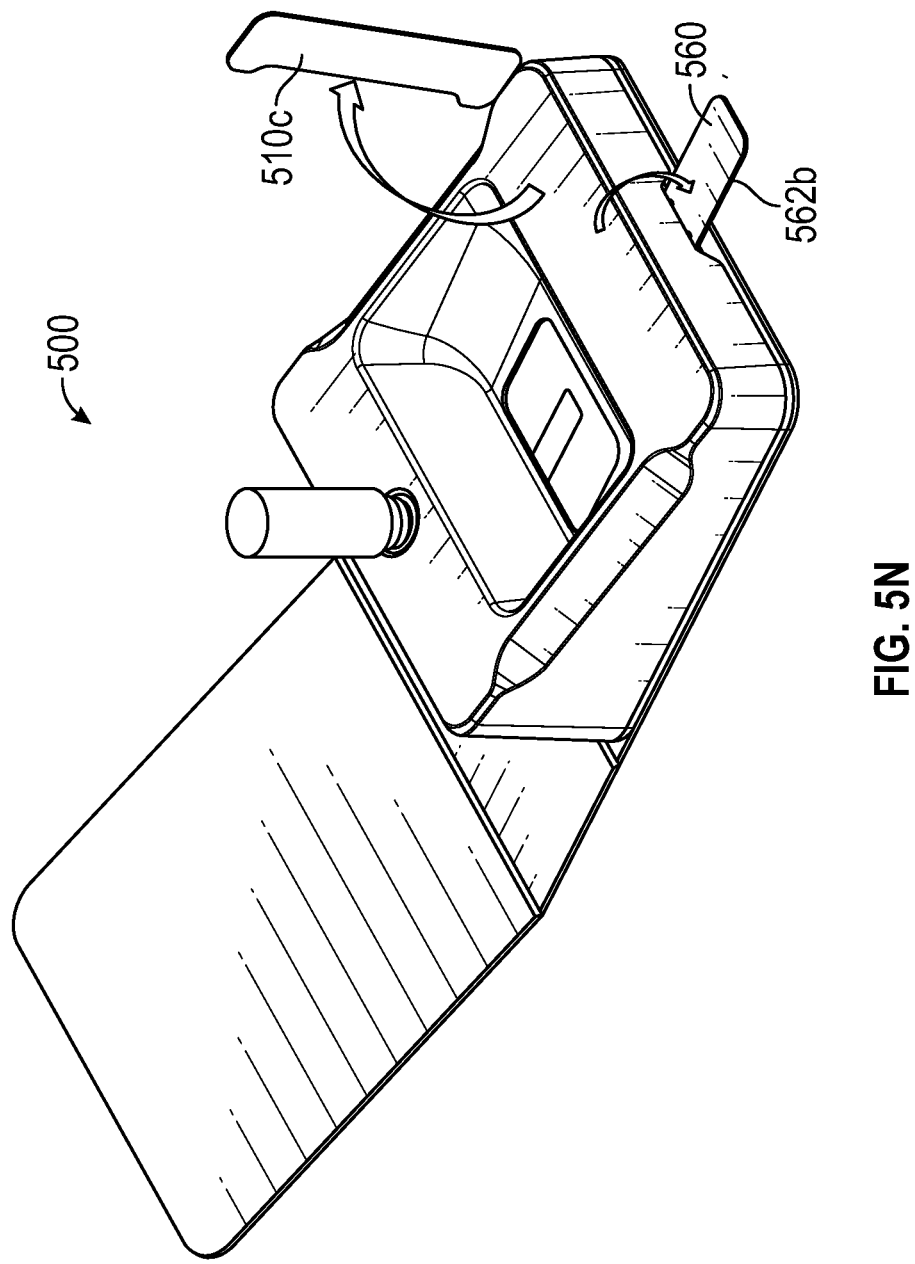
Figure 50:
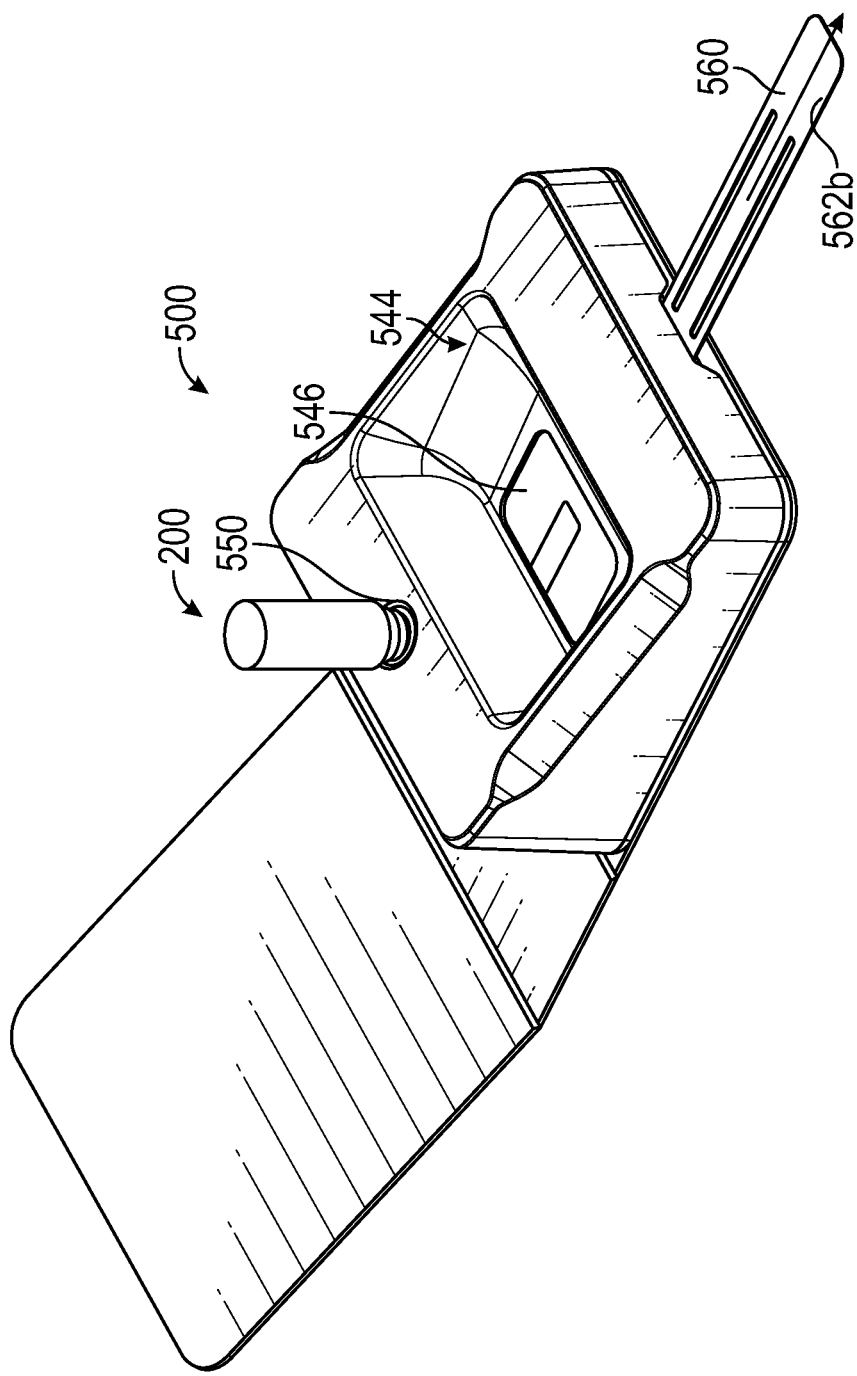

Referring next to FIG. 5N, the user can remove the third sealing label 510*c* to release and/or expose the second end 562*b* of the sealing element 560.

Referring next to FIG. 5O, the user can grip the second end 562*b* of the sealing element 560 and pull the sealing element 560 away from the rest of the device 500 to release the eluted sample onto the test strip 102, as previously described with reference to FIGS. 5H and 5I. This process can be performed while the sample swab 200 remains in the fluid reservoir 550, or the sample swab 200 can be removed from the fluid reservoir 550 beforehand. The user can then view the test results via the window 546 in the recess 544 of the device 500.

Figure 6:
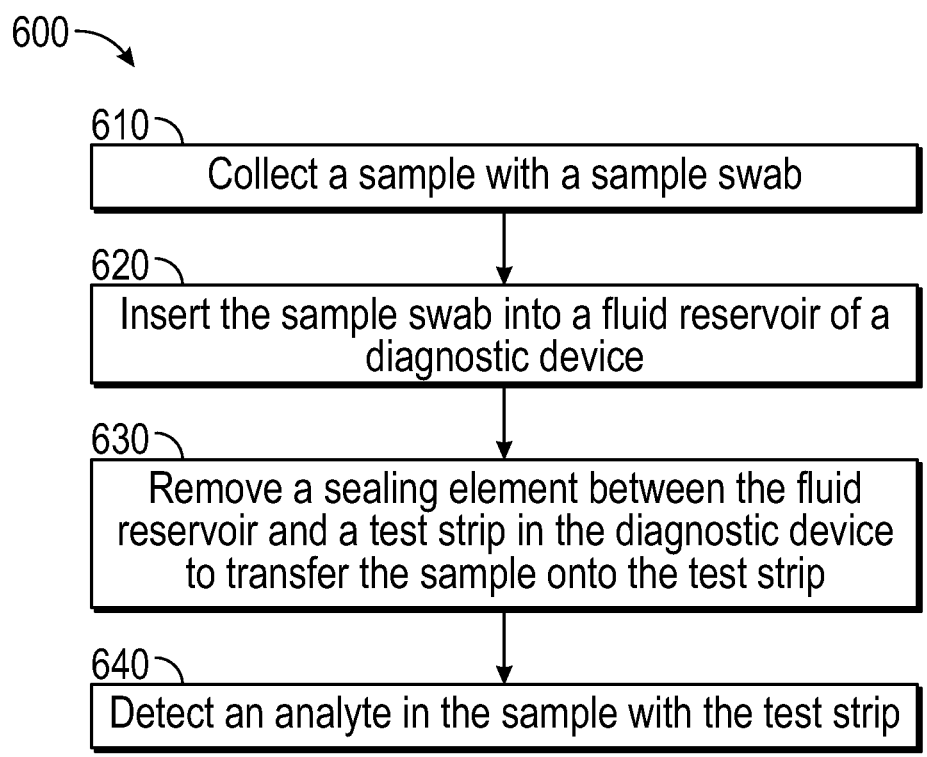
FIG. 6 is a flow diagram illustrating a method for analyzing a sample from a patient, in accordance with embodiments of the present technology.

FIG. 6 is a flow diagram illustrating a method 600 for analyzing a sample from a patient, in accordance with embodiments of the present technology. The method 600 can be performed using any of the devices described herein, such as the diagnostic device 500 of FIGS. 5A-5O and/or the sample swab 200 of FIG. 2.

The method 600 begins at step 610 with collecting a sample with a sample swab (e.g., the sample swab 200 of FIG. 2). Step 610 can be identical or similar to step 410 of the method 400 of FIG. 4.

At step 620, the method 600 includes inserting the sample swab into a fluid reservoir of a diagnostic device (e.g., as shown in FIG. 5M). As previously described with reference to FIGS. 5F-5I, the fluid reservoir can be integrated into a housing or other portion of the diagnostic device. The fluid reservoir can contain a solution for hydrating the sample swab, lysing or otherwise interacting with a sample on the swab, etc. In some embodiments, step 620 includes immersing the sample swab in the solution for a particular period of time, e.g., no more than 1 second, 5 seconds, 10 seconds, or 30 seconds. Optionally, step 620 can further include squeezing the sample out of the sample swab via one or more extraction structures (e.g., the ribs 568 of the device 500 of FIGS. 5A-5O). The user can direct the sample swab against the extraction structures (e.g., by rotating the sample swab, moving the swab up and down, etc.) to facilitate sample elution.

At step 630, the method 600 continues with removing a sealing element between the fluid reservoir and a test strip in the diagnostic device (e.g., as shown in FIG. 5O). As previously described with reference to FIGS. 5H and 5I, the sealing element can cover a bottom portion of the fluid reservoir so the solution is sealed within the fluid reservoir. Once the sample has been eluted from the sample swab into the solution, the sealing element can be removed so the eluted sample flows out of the fluid reservoir and onto the test strip.

At step 640, the method 600 includes detecting an analyte in the sample with the test strip. Step 640 can be identical or similar to step 440 of the method 400 of FIG. 4.

The various embodiments described herein can be combined with each other in many different ways, e.g., any of the features of the device 100 of FIGS. 1A-1G can be combined with any of the features of the device 500 of FIGS. 5A-5O. For example, the device 100 can be modified to include an aperture in the fluid reservoir 130 and a sealing element covering the aperture, e.g., similar to the second aperture 558 and sealing element 560 of the device 500. As another example, the device 500 can be modified to include an aperture spaced apart from the fluid reservoir and configured to direct the sample swab into direct contact with the test strip, e.g., similar to the aperture 150 of the device 100.

In some embodiments, the devices of the present technology are provided as part of a kit for detecting an analyte in a patient sample, e.g., for the purposes of determining whether the patient has COVID-19 or another disease. A kit configured in accordance with embodiments of the present technology can include a diagnostic device, such as the device 100 of FIGS. 1A-1G or the device 500 of FIGS. 5A-5O. The kit can include a test strip housed within the device. The kit can also include at least one sample swab (e.g., the sample swab 200 of FIG. 2). The kit can also include instructions for operating the diagnostic device, e.g., in accordance with the method 400 of FIG. 4 or the method 600 of FIG. 6.

The devices and associated methods of the present technology can be used to detect many different types of analytes in a patient sample. In some embodiments, for example, the present technology can be used to detect COVID-19 from a saliva sample or a specimen from the anterior nares, mid turbinate, nasopharynx or the oropharynx. In such embodiments, the test strip in the diagnostic device can be an LFA test strip with one or more lines (e.g., dual line) having two or more antibodies that accurately detect SARS-CoV-2 virus (or antigen thereof, such as a nucleocapsid antigen) with a high signal-to-noise ratio (e.g., a strong signal with relatively low noise).

In some embodiments, the present technology uses various combinations of the following antibodies to detect SARS-CoV-2 virus or an antigen thereof: Exonbio 3E6; Exonbio 5B1; Exonbio 5C3; Exonbio 3H1; Sinobiological 40143-MM08; Sinobiological 40143-MM05; Sinobiological 40143-R004; Genetex 5712; National University of Singapore antibody LSI-011; National University of Singapore antibody LSI-010; National University of Singapore antibody LSI-002; National University of Singapore antibody LSI-014; National University of Singapore antibody LSI-016; Meridian 9547; Meridian 9548; Meridian 9550; and Meridian 9551. These antibodies can be matched in antibody pairs or combination of three or more of the antibodies.

Any of the foregoing antibody combinations can be conjugated with nanoparticles (e.g., 150 nm gold nanoshells from nanoComposix, Inc., a California company) and a buffer. Suitable buffers include those manufactured by Fantibody, a Chongging, China company, or a mixture of Tris and Triton X100 manufactured by nanoComposix, Inc with NaCl. Other buffers may be suitable as well.

Although certain embodiments herein are described with reference to diagnosing a patient with COVID-19, in other embodiments, the present technology can be used to diagnose diseases and/or other applications involving detection of analytes in a sample. For example, the devices, methods, and kits described herein can incorporate test strips and/or other reagents configured to detect at least one analyte (e.g., an antigen) associated with any of the following diseases: chicken pox, chlamydia, Clostridium difficile infection, cytomegalovirus (CMV) infection, dengue fever, Ebola, enteric disease, giardiasis, gonorrhea, herpes simplex virus (HSV) infection, human immunodeficiency virus (HIV) infection, human papillomavirus (HPV) infection, influenza (e.g., influenza A, influenza B, influenza C), Lyme disease, malaria, measles, mononucleosis, mumps, norovirus infection, pneumonia, respiratory syncytial virus (RSV) infection, rubella, shingles, staph infection (e.g., methicillin-resistant *Staphylococcus aureus* (MRSA) infection), streptococcal pharyngitis, syphilis, tuberculosis, West Nile fever, or Zika fever.

The following examples provide further representative embodiments of the present technology.

EXAMPLES

1. A device for analyzing a sample, the device comprising:
   a housing base configured to retain a test strip; and
   a housing cover configured to couple to the housing base to at least partially enclose the test strip, wherein the housing cover includes:
     a fluid reservoir configured to hold a solution for hydrating a sample swab, and
     an aperture configured to permit transfer of a sample from the sample swab onto the test strip.

2. The device of example 1, wherein the aperture is spaced apart from the fluid reservoir and configured to receive the sample swab and direct the sample swab into direct contact with the test strip.

3. The device of example 2 wherein the housing cover includes a raised portion, and the aperture is in the raised portion.

4. The device of example 3 wherein the raised portion has a height of at least 2 cm above a remaining portion of the housing cover.

5. The device of example 3 or example 4 wherein the raised portion includes an interior cavity, and the fluid reservoir is within the interior cavity.

6. The device of any one of examples 2-5 wherein the housing cover includes a guide structure near the aperture and configured to limit an insertion depth of the sample swab into the aperture.

7. The device of example 6 wherein the guide structure includes a stop surface at least partially surrounding the aperture, and the stop surface is configured to engage the sample swab to limit the insertion depth.

8. The device of example 7, further comprising the sample swab, wherein the sample swab includes a handle portion configured to engage the stop surface.

9. The device of example 6 wherein the guide structure is configured to control an insertion angle of the sample swab so the sample swab is substantially vertical when in direct contact with the test strip.

10. The device of any one of examples 2-9 wherein:
   the housing cover includes an inner surface having one or more struts, and
   when the housing cover is coupled to the housing base, the one or more struts apply pressure to a portion of the test strip to facilitate fluid flow therethrough.

11. The device of example 1 wherein:
   the aperture is at a bottom portion of the fluid reservoir and above a portion of the test strip; and
   the device further comprises a sealing element covering the aperture and separating the fluid reservoir from the test strip, wherein the sealing element is configured to be removable to allow the sample to flow from the fluid reservoir onto the test strip.

12. The device of example 11 wherein the fluid reservoir includes at least one extraction structure configured to contact the sample swab to enhance sample elution from the sample swab.

13. The device of example 12 wherein the at least one extraction structure includes a plurality of vertical ribs.

14. The device of any one of examples 11-13, further comprising the sample swab, wherein the sample swab includes a handle portion configured to engage the fluid reservoir.

15. The device of example 14 wherein engagement between the handle portion and the fluid reservoir limits an insertion depth of the sample swab.

16. The device of example 14 or example 15 wherein engagement between the handle portion and the fluid reservoir constrains the sample swab to a substantially vertical orientation.

17. The device of any one of examples 11-16 wherein the housing cover includes a recess configured to store the sample swab.

18. The device of example 17 wherein the recess includes a second aperture configured to expose a readout portion of the test strip.

19. The device of any one of examples 11-18 wherein the sealing element includes a first end portion configured to cover the aperture and a second end portion extending outside the housing cover and the housing base, the second end portion being configured as a pull tab for removing the first end portion from the aperture.

20. The device of any one of examples 1-19, further comprising the solution for hydrating the sample swab, wherein the solution is in the fluid reservoir and the fluid reservoir is covered by a sealing element.

21. The device of any one of examples 1-20, further comprising the test strip, wherein the test strip includes at least one reagent configured to detect SARS-CoV-2.

22. The device of example 21 wherein the housing cover includes a window configured to expose a readout portion of the test strip.

23. A kit for detecting SARS-CoV-2 in a sample from a patient's nasal cavity, the kit comprising:
   a sample swab including:
      a swab portion configured to collect a sample from the patient's nasal cavity, and
      a handle portion coupled to the swab portion, the handle portion being configured to limit an insertion depth of the swab portion into the patient's nasal cavity;
   a test strip including at least one reagent configured to detect SARS-CoV-2; and
   a diagnostic device including:
      a housing base configured to retain the test strip;
      a housing cover configured to couple to the housing base to at least partially enclose the test strip, wherein the housing cover includes:
         a fluid reservoir holding a solution for hydrating the swab portion, and
         an aperture configured to permit transfer of the sample from the swab portion onto the test strip.

24. The kit of example 23 wherein the aperture is spaced apart from the fluid reservoir and configured to receive the swab portion and direct the swab portion into direct contact with the test strip.

25. The kit of example 24 wherein the housing cover includes a guide structure near the aperture, and the guide structure includes a stop surface configured to engage the handle portion to control an insertion depth and an insertion angle of the swab portion into the aperture.

26. The kit of example 24 or example 25 wherein the housing cover includes a raised portion and a flattened portion.

27. The kit of example 26 wherein the aperture and the fluid reservoir are in the raised portion of the housing cover.

28. The kit of example 23 wherein:
   the aperture is at a bottom portion of the fluid reservoir and above a portion of the test strip, and
   the diagnostic device includes a sealing element covering the aperture and separating the fluid reservoir from the test strip, wherein the sealing element is configured to be removable to allow the sample to flow from the fluid reservoir onto the test strip.

29. The kit of example 28 wherein the housing cover includes a recess configured for storing the sample swab.

30. The kit of example 29, further comprising a second aperture within the recess and configured to expose a readout portion of the test strip.

31. The kit of example 29 or example 30, further comprising:
   a first label covering the fluid reservoir;
   a second label covering the recess; and
   a third label preventing removal of the sealing element from the diagnostic device.

32. The kit of any one of examples 23-31 wherein the swab portion has a length less than or equal to 2 cm.

33. The kit of any one of examples 23-32 wherein the swab portion has a length configured for collecting an anterior nasal sample.

34. A method for analyzing a sample from a patient, the method comprising:
   collecting the sample from the patient with a sample swab;
   inserting the sample swab into a fluid reservoir to hydrate the sample, wherein the fluid reservoir is integrated into a housing of a diagnostic device; and
   depositing the sample onto a test strip retained within the housing of the diagnostic device via an aperture in the housing that exposes a portion of the test strip.

35. The method of example 34 wherein the aperture is spaced apart from the fluid reservoir, and wherein depositing the sample onto the test strip includes inserting the sample swab into the aperture and into direct contact with the portion of the test strip.

36. The method of example 35 wherein the sample swab is in a substantially vertical orientation when placed into direct contact with the test strip.

37. The method of example 36, further comprising engaging a portion of the sample swab with the housing to maintain the sample swab in the substantially vertical orientation.

38. The method of any one of examples 35-37, further comprising engaging a portion of the sample swab with the housing to limit an amount of contact force between the sample swab and the test strip.

39. The method of example 34 wherein the aperture is between the fluid reservoir and the portion of the test strip, and wherein depositing the sample onto the test strip includes removing a sealing element covering the aperture so the sample flow through the aperture and onto the portion of the test strip.

40. The method of example 39 wherein removing the sealing element comprises pulling the sealing element at least partially out of the housing.

41. The method of example 39 or example 40 wherein the sample swab remains in the fluid reservoir while the sealing element is removed.

42. The method of any one of examples 39-41, further comprising engaging a portion of the sample swab with the housing to maintain the sample swab in a substantially vertical orientation within the fluid reservoir.

43. The method of any one of examples 39-42, further comprising engaging a portion of the sample swab with the housing to limit an insertion depth of the sample swab into the fluid reservoir.

44. The method of any one of examples 34-43 wherein the sample includes an anterior nasal sample from the patient.

45. The method of any one of examples 34-44 wherein the sample swab includes a handle portion configured to restrict an insertion depth of the sample swab into the patient's body.

46. The method of any one of examples 34-45, further comprising detecting at least one analyte in the sample with the test strip.

47. The method of example 46 wherein the at least one analyte includes a SARS-CoV-2 nucleocapsid antigen.

48. A device for analyzing a sample, the device comprising:
a housing base configured to retain a test strip;
a housing cover configured to couple to the housing base to at least partially enclose the test strip, wherein the housing cover includes;
a fluid reservoir configured to hold a solution for hydrating a sample swab, and
an aperture spaced apart from the fluid reservoir and configured to receive the sample swab and direct the sample swab into direct contact with the test strip.

49. A kit for detecting SARS-CoV-2 in a sample from a patient's nasal cavity, the kit comprising:
a sample swab including:
a swab portion configured to collect a sample from the patient's nasal cavity, and
a handle portion coupled to the swab portion, the handle portion being configured to limit an insertion depth of the swab portion into the patient's nasal cavity;
a test strip including at least one reagent configured to detect SARS-CoV-2; and
a diagnostic device including:
a housing base configured to retain the test strip;
a housing cover configured to couple to the housing base to at least partially enclose the test strip, wherein the housing cover includes:
a fluid reservoir holding a solution for hydrating the swab portion,
an aperture spaced apart from the fluid reservoir and configured to receive the swab portion and direct the swab portion into direct contact with the test strip, and
a guide structure near the aperture, wherein the guide structure includes a stop surface configured to engage the handle portion to control an insertion depth and an insertion angle of the swab portion into the aperture.

50. A method for analyzing a sample from a patient, the method comprising:
collecting the sample from the patient with a sample swab;
inserting the sample swab into a fluid reservoir to hydrate the sample, wherein the fluid reservoir is integrated into a housing of a diagnostic device; and
placing the sample swab into direct contact with a test strip retained within the housing of the diagnostic device so the sample is transferred from the sample swab to the test strip.

51. A device for analyzing a sample, the device comprising:
a housing base configured to retain a test strip;
a housing cover configured to couple to the housing base to at least partially enclose the test strip, wherein the housing cover includes;
a fluid reservoir configured to hold a solution for eluting a sample from a sample swab, and
an aperture at a bottom portion of the fluid reservoir and above a portion of the test strip; and
a sealing element covering the aperture and separating the fluid reservoir from the test strip, wherein the sealing element is configured to be removable to allow the eluted sample to flow from the fluid reservoir onto the test strip.

52. A kit for detecting SARS-CoV-2 in a sample from a patient's nasal cavity, the kit comprising:
a sample swab including:
a swab portion configured to collect a sample from the patient's nasal cavity, and
a handle portion configured to limit an insertion depth of the swab portion into the patient's nasal cavity;
a test strip including at least one reagent configured to detect SARS-CoV-2; and
a diagnostic device including:
a housing base configured to retain the test strip;
a housing cover configured to couple to the housing base to at least partially enclose the test strip, wherein the housing cover includes:
a fluid reservoir holding a solution for eluting the sample from the sample swab, and
an aperture at a bottom portion of the fluid reservoir and above a portion of the test strip, and
a sealing element covering the aperture and separating the fluid reservoir from the test strip, wherein the sealing element is configured to be removable to allow the eluted sample to flow from the fluid reservoir onto the test strip.

53. A method for analyzing a sample from a patient, the method comprising:
collecting the sample from the patient with a sample swab;
inserting the sample swab into a fluid reservoir to elute the sample, wherein the fluid reservoir is integrated into a housing of a diagnostic device; and removing a sealing element between the fluid reservoir and a test strip within the housing of the device, wherein the removal of the sealing element releases the eluted sample onto the test strip.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for analyzing a sample, the device comprising:
   a test strip including at least one reagent configured to detect SARS-CoV-2;
   a housing base configured to retain the test strip; and
   a housing cover configured to couple to the housing base to at least partially enclose the test strip, wherein the housing cover includes;
      a fluid reservoir configured to hold a solution for hydrating a sample swab, and
      an aperture spaced apart from the fluid reservoir and configured to receive the sample swab and direct the sample swab into direct contact with the test strip.

2. The device of claim 1 wherein the housing cover includes a raised portion, and the aperture is in the raised portion.

3. The device of claim 2 wherein the raised portion has a height of at least 2 cm above a remaining portion of the housing cover.

4. The device of claim 2 wherein the raised portion includes an interior cavity, and the fluid reservoir is within the interior cavity.

5. The device of claim 1 wherein the housing cover includes a guide structure near the aperture and configured to limit an insertion depth of the sample swab into the aperture.

6. The device of claim 5 wherein the guide structure includes a stop surface at least partially surrounding the aperture, and the stop surface is configured to engage the sample swab to limit the insertion depth.

7. The device of claim 6, further comprising the sample swab, wherein the sample swab includes a handle portion configured to engage the stop surface.

8. The device of claim 7 wherein the guide structure is configured to control an insertion angle of the sample swab so the sample swab is substantially vertical when in direct contact with the test strip.

9. The device of claim 7 wherein the handle portion is configured to restrict an insertion depth of the sample swab into a patient's body.

10. The device of claim 1 wherein:
    the housing cover includes an inner surface having one or more struts, and
    when the housing cover is coupled to the housing base, the one or more struts apply pressure to a portion of the test strip to facilitate fluid flow therethrough.

11. The device of claim 1, further comprising the solution for hydrating the sample swab, wherein the solution is in the fluid reservoir and the fluid reservoir is covered by a sealing element.

12. The device of claim 1 wherein the housing cover includes a window configured to expose a readout portion of the test strip.

13. A device for analyzing a sample, the device comprising:
    a test strip including at least one reagent configured to detect SARS-CoV-2;
    a housing base configured to retain the test strip;
    a housing cover configured to couple to the housing base to at least partially enclose the test strip, wherein the housing cover includes;
       a fluid reservoir configured to hold a solution for eluting a sample from a sample swab, and
       an aperture at a bottom portion of the fluid reservoir and above a portion of the test strip; and
    a slidable sealing element covering the aperture and configured to move between a first position in which the sealing element separates the fluid reservoir from the test strip and a second position in which the sealing element allows eluted sample to flow from the fluid reservoir onto the test strip.

14. The device of claim 13 wherein the fluid reservoir includes at least one extraction structure configured to contact the sample swab to enhance sample elution from the sample swab.

15. The device of claim 14 wherein the at least one extraction structure includes a plurality of vertical ribs.

16. The device of claim 13, further comprising the sample swab, wherein the sample swab includes a handle portion configured to engage the fluid reservoir.

17. The device of claim 16 wherein engagement between the handle portion and the fluid reservoir limits an insertion depth of the sample swab.

18. The device of claim 16 wherein engagement between the handle portion and the fluid reservoir constrains the sample swab to a substantially vertical orientation.

19. The device of claim 16 wherein the handle portion is configured to restrict an insertion depth of the sample swab into a patient's body.

20. The device of claim 13 wherein the housing cover includes a recess configured to store the sample swab.

21. The device of claim 20 wherein the recess includes a window configured to expose a readout portion of the test strip.

22. The device of claim 20, further comprising:
a first label covering the fluid reservoir;
a second label covering the recess; and
a third label preventing removal of the sealing element from the device.

23. The device of claim 13 wherein the sealing element includes a first end portion configured to cover the aperture and a second end portion extending outside the housing cover and the housing base, the second end portion being configured as a pull tab for removing the first end portion from the aperture.

24. A device for analyzing a sample, the device comprising:
a test strip including at least one reagent configured to detect SARS-CoV-2;
a housing base configured to retain the test strip; and
a housing cover configured to couple to the housing base to at least partially enclose the test strip, wherein the housing cover includes:
a fluid reservoir configured to hold a solution for hydrating a sample swab, wherein the fluid reservoir is spaced laterally apart from the test strip along the length and width of the housing cover, and
an aperture configured to permit transfer of a sample from the sample swab onto the test strip.

25. The device of claim 24, wherein the aperture is spaced apart from the fluid reservoir and configured to receive the sample swab and direct the sample swab into direct contact with the test strip.

26. The device of claim 25 wherein the housing cover includes a raised portion, and the aperture is in the raised portion.

27. The device of claim 26 wherein the raised portion includes an interior cavity, and the fluid reservoir is within the interior cavity.

* * * * *